United States Patent [19]

Hase

[11] Patent Number: 5,714,676
[45] Date of Patent: Feb. 3, 1998

[54] METHOD AND APPARATUS FOR ANALYZING GAS COMPONENTS AND APPARATUS FOR COLLECTING SAMPLE GASES

[75] Inventor: Ushio Hase, Tokyo, Japan

[73] Assignee: NEC Corporation, Tokyo, Japan

[21] Appl. No.: 469,877

[22] Filed: Jun. 6, 1995

[30] Foreign Application Priority Data

Jun. 6, 1994 [JP] Japan .................................. 6-123418
Feb. 14, 1995 [JP] Japan .................................. 7-024871

[51] Int. Cl.$^6$ .................................................. G01N 30/20
[52] U.S. Cl. ................................. 73/23.41; 73/864.83
[58] Field of Search ...................... 73/23.41, 864.83, 73/864.84

[56] References Cited

U.S. PATENT DOCUMENTS

| | | | |
|---|---|---|---|
| 4,472,354 | 9/1984 | Passell et al. | 73/23.41 X |
| 5,073,502 | 12/1991 | Steele | 73/23.41 X |
| 5,152,176 | 10/1992 | Bryselbout et al. | 73/23.41 |

OTHER PUBLICATIONS

P. Lindgren et al., "Measurement of Atmospheric Sulfur Dioxide by Diffusion Scrubber Coupled Ion Chromatography", Analytical Chemisty, Jan. 1, 1989, vol. 61, No. 1, pp. 19–24.

Z. Genfa et al., "Measurement of Atmospheric Ammonia", Environ. Sci. Technol., Dec. 1989, vol. 23, No. 12, pp. 1467–1474.

S. Tanaka, "New Measurement Techinque of Acidic Gas in Atmosphere of Cities Using an Ion Chromatography", Feb. 1992, pp. 75–85, (in Japanese).

*Primary Examiner*—Thomas P. Noland
*Attorney, Agent, or Firm*—Young & Thompson

[57] ABSTRACT

A gas component analyzing system having a diffusion scrubber and a chromatograph wherein a flow passage switch valve and a sample injection valve are switched to form a non-circulation flow passage for feeding an absorption liquid into the diffusion scrubber so that absorption liquid captures sample gas components until the sample gas components come into an equilibrium state. Then, both the above valves are switched to form a circulation flow passage for feeding the absorption liquid into a concentration column. Then, both the above valves are further switched to form the non-circulation flow passage to elute the sample gas components for subsequent detection thereof by the chromatograph.

25 Claims, 8 Drawing Sheets

METHOD AND APPARATUS FOR ANALYZING GAS COMPONENTS AND APPARATUS FOR COLLECTING SAMPLE GASES

BACKGROUND OF THE INVENTION

The present invention relates to a method and an apparatus for analyzing gases with a continuous monitoring of volatile components in a clean atmosphere and an apparatus for collecting gas samples for a subsequent gas analysis.

In the prior art, an analysis of gas components in atmosphere is carried out by collection of gas samples and subsequent various analyses in an analyzing room. A specific gas component analysis of gas may, however, be carried out by establishing sensors and recorders in the field to monitor the gas components. In the normal sample collection in the field, gas components are absorbed into either an extracting liquid containing an absorbent or an absorbing liquid for analysis.

Liquid chromatographs such as high speed liquid chromatograph or ion-chromatograph have features of capability of highly sensitive analyses of a plurality of components in the liquid by one time sample injection. Particularly, an ion chromatograph for exclusively analyzing inorganic components has come to be widely used as being available to analyze readily anion components, although it seems complicated to analyze the anion components by other analysis methods. An analysis for acidic gas components is carried out by the sampling and subsequent analysis of the absorption liquid and the extracting liquid containing the absorbent by the ion chromatograph.

In the method by use of the absorption liquid, there had been widely used a method of put a predetermined amount of the absorption liquid into either a bubbler or an impinger for absorption of atmosphere and bubbling thereof to allow the components to dissolve into the liquid until another gas sampling method which uses a gas transparent film was developed. This another method is disclosed in Analytical Chemistry, Vol. 61, No. 1, January 1998 entitled "measurement of atmospheric sulfur dioxide by diffusion scrubber coupled ion chromatography".

FIG. 1 illustrates this conventional analyzing apparatus using the gas transparent film. The conventional apparatus comprises a sample collection section and a sample analyzing section. The sample collection section mainly comprises a diffusion scrubber 101. The diffusion scrubber 101 comprises outer and inner tubes 105 and 104. The absorption liquid or an extraction liquid containing the absorbent flow through between the inner and outer tubes 104 and 105. The inner tube 104 comprises micro-porous membrane tube which allows molecules of the gases to penetrate through the micro-porous into between the inner and outer tubes 104 and 105 but may prevent dust particles in atmosphere from penetrating into between the inner and outer tubes 104 and 105. ThE micro-porous membrane tube as the inner tube 104 may also prevent the absorption liquid from seeping into the inside of the inner tube 104. The micro-porous membrane tube 104 may isolate the atmosphere from the absorption liquid but have the gas molecules free to penetrate into the absorption liquid. The absorption liquid is fed from a scrubber liquid reservoir 141 through a scrubber liquid pump 115 into the diffusion scrubber 101. The sampling gas is fed from a gas suction port 113 through a gas sampling pump 112 and a flow meter 116 into the diffusion scrubber 101. The sampling gas is then transmitted through the inside of the inner tube 104 into a discharge port. The absorption liquid is transmitted through the outside of the inner tube 104 but the inside of the outer tube 105 so as to capture the gas molecules penetrated through the micro-porous.

The diffusion scrubber 101 is connected to the ion chromatograph 130 for analyzing the gas components. The absorption liquid having captured the gas molecules in the diffusion scrubber is then fed through a sample injection valve 111 involved in the ion chromatograph 130 into a sample loop 114 in which the absorption liquid is reserved for future analysis of the gas components. In this case, the sample injection valve 111 takes one state represented by the real lines in FIG. 1. The ion chromatograph has a liquid reservoir 136 and a liquid pump 131 for feeding the liquid into a guard column 132 separately from the absorption liquid reserved in the sampling loop 114. The guard column 132 is connected to a separation column 133 which is further connected to a suppresser 134. The suppresser 134 is connected to a detector 135 for detecting an electrical conductivity.

For analyzing the gas components, the sample injection valve 111 will take another state represented by the dotted lines in FIG. 1 so that the absorption liquid into which the gas molecules have been captured is fed from the sampling loop 114 through the guard column 132, the isolation column 133, the suppresser 134 and the electrical conductivity detector 135 for analyzing the gas components.

Another conventional apparatus for sampling and analyzing the gas components has been known in the art, which is illustrated in FIG. 2. The another conventional apparatus has an improvement in a sensitivity of the gas components. The sample injection valve is provided with a concentration column in place of the sampling loop. This another conventional apparatus is disclosed in February 1992, PPM, pp. 75–85.

The another conventional apparatus comprises a sample collection section and a sample analyzing section. The sample collection section mainly comprises a diffusion scrubber 151. The diffusion scrubber 151 comprises outer and inner tubes 155 and 154. The absorption liquid or an extraction liquid containing the absorbent flow through between the inner and outer tubes 154 and 155. The inner tube 154 comprises micro-porous membrane tube which allows molecules of the gases to penetrate through the micro-porous into between the inner and outer tubes 154 and 155 but may prevent dust particles in atmosphere from penetrating into between the inner and outer tubes 154 and 155. The micro-porous membrane tube as the inner tube 154 may also prevent the absorption liquid from seeping into the inside of the inner tube 154. The micro-porous membrane tube 154 may isolate the atmosphere from the absorption liquid but have the gas molecules free to penetrate into the absorption liquid. The absorption liquid is fed from a scrubber liquid reservoir 191into the diffusion scrubber 151. The sampling gas is introduced from a gas suction port 163 of the diffusion scrubber 151 into the inside of the inner tube 154. The sampling gas is discharged from an opposite end to the section port 163 in the diffusion scrubber 151 and then fed through a three way valve 171 and a flow meter 166 into a sampling gas pump 162 for discharge from this system. The absorption liquid is transmitted through the outside of the inner tube 154 but the inside of the outer tube 155 so as to capture the gas molecules penetrated through the micro-porous.

The diffusion scrubber 151 is connected through an absorption liquid pump 165 to the ion chromatograph 180 for analyzing the gas components. The absorption liquid having captured the gas molecules in the diffusion scrubber 151 is then fed through the sample liquid pump 165 into a sample injection valve 161 involved in the ion chromatograph 180. The sample liquid is then fed into a sample loop 114 in which the absorption liquid or the sample liquid is reserved for future analysis of the gas components.

The three way valve 171 is controlled by a timer 172 for controlling a sampling time for sampling the gases. The sample injection valve 161 161 switches between two different states by an action of an actuator 174. The actuator 174 is controlled by both the timer 172 and another timer 173. When the sampling injection valve 161 takes one state represented by the real line in FIG. 2, the absorption liquid having captured the sample gases is fed into the concentration column 164 to be reserved therein for future analysis of the gas components. In the concentration column 164, the gas components in the absorption liquid are concentrated. The sample injection valve 161 switches to take another state represented by the dotted lines in FIG. 2 so that the absorption liquid having captured the sample gases comes to be fed from the concentration column 164 into a column oven 187. An eluate reserved in an eluate reservoir 186 is fed through an eluate pump 181 into a column oven 187. The concentrated components of the gases captured in the absorption liquid is also fed from the concentration column 164 into the column oven 187 during which the concentrated components thereof show an elution into the eluate fed from the elution reservoir 186. The eluted sample is then fed through a guard column 182, an isolation column 183, a suppresser 184 and an electrical conductivity detector 185 in turn during which the gas components in the absorption liquid are analyzed.

The sample injection valve 161 is controlled by the timers 172 and 173 to switch between the two states at a constant time interval so that there may be monitored a variation in gas components to be analyzed as a time passes. For example, a nitric acid component may be measured one time per one hour.

The above two conventional apparatus have the following disadvantages. It is a serial fact that impurities in the atmosphere in a clean room on a production line provides considerable influences to reliability and yield of the products. From this viewpoint, it is required to analyze the gases at a high sensitivity. It is further required to analyze the gases within a short time. It is furthermore required to allow the gas analyzer to perform for a long time without maintenance.

The conventional apparatus provided with a sampling loop illustrated in FIG. 1 has an insufficient sensitivity.

The another conventional apparatus provided with a concentration column illustrated in FIG. 2 has a feature that a long time sampling allows an improvement in sensitivity thereof. However, no-load running test value is also increased. For analyzing a small quantity of the gas component, a long time sampling is carried out, resulting, however, in no improvement in a ratio (S/B) of an intensity (S) of the sample component to an intensity (B) of the no-load running text value During the transmission of the absorption liquid through the diffusion scrubber, the absorption liquid may absorb not only the analyzing components but also atmospheric components, thereby the atmospheric components show foam in the pump, resulting in a flow rate variation. From this facial matter, it seems difficult to put the gas analyzer in operation for a long time by unmanned control.

SUMMARY OF THE INVENTION

Accordingly, it is an object of the present invention to provide a novel apparatus for collecting gas components, said apparatus being free from any problems as described above.

It is another object of the present invention to provide a novel apparatus for analyzing gas components free from any problem as described above.

It is still another object of the present invention to provide a novel apparatus for analyzing gas components having an improved high sensitivity.

It is yet another object of the present invention to provide a novel apparatus for analyzing volatile gas components at a high sensitivity.

It is a further object of the present invention to provide a novel method for analyzing gas components free from any problem as described above.

It is a still further object of the present invention to provide a novel method for analyzing gas components having an improved high sensitivity.

It is yet a further object of the present invention to provide a novel method for analyzing volatile gas components at a high sensitivity.

It is moreover object of the present invention to provide a system including a diffusion scrubber and a chromatograph for analyzing gas components wherein a flow passage switch valve and a sample injection valve are switched to form a non-circulation flow passage for feeding an absorption liquid into the diffusion scrubber so that absorption liquid captures sample gas components until the same gas components come into an equilibrium state and thereafter the above both valves are switched to form a circulation flow passage for feeding the absorption liquid into a concentration column and subsequently both the above two vales are again switched to form the non-circulation flow passage to elute the sample gas components for detection thereof by the chromatograph.

The above and other objects, features and advantages of the present invention will be apparent from the following descriptions.

BRIEF DESCRIPTIONS OF THE DRAWINGS

Preferred embodiments of the present invention will hereinafter be described in detail with reference to the accompanying drawings.

DESCRIPTIONS OF THE INVENTION

Figure 1:
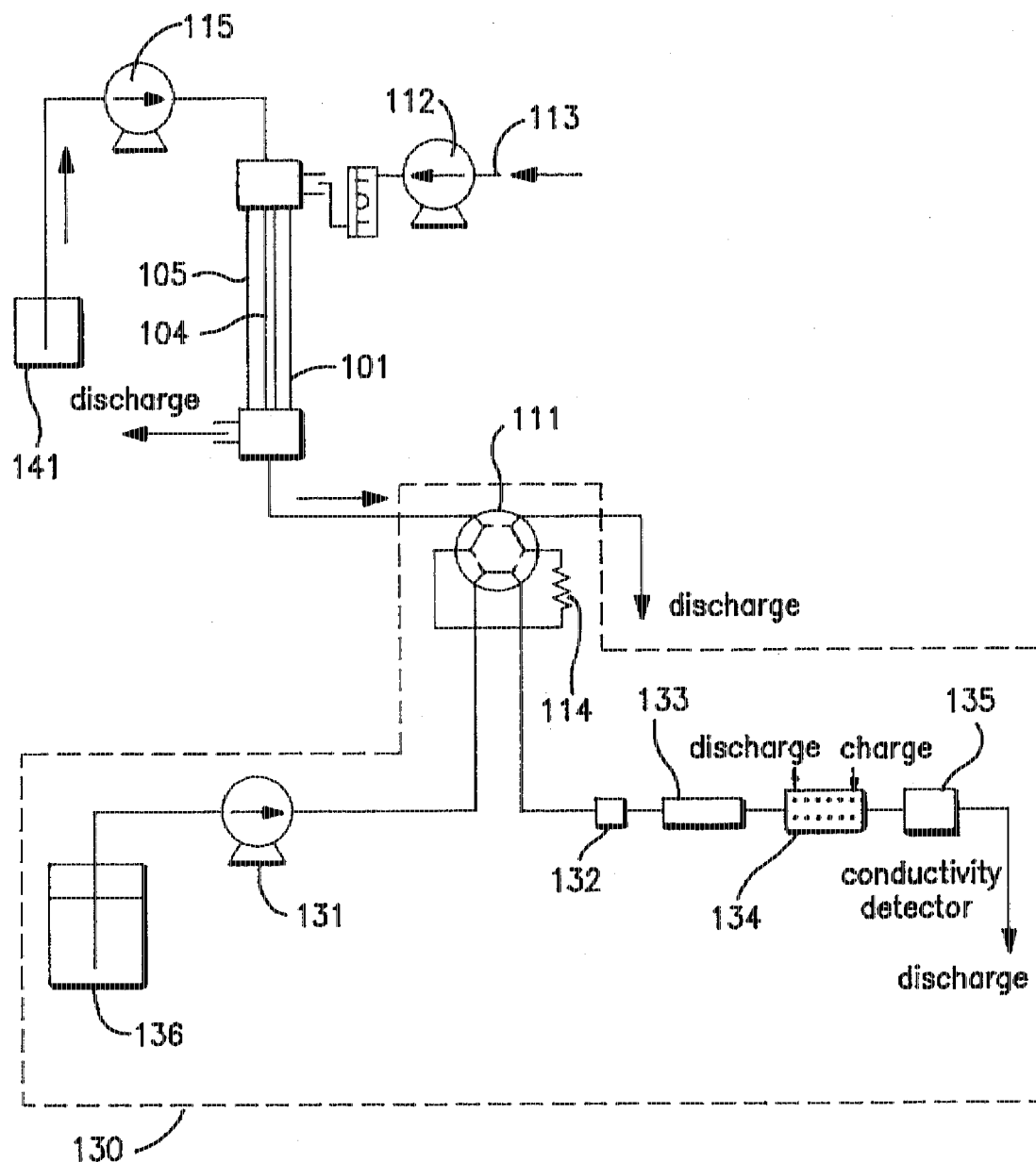
FIG. 1 is a diagram illustrative of the conventional gas component analyzing system having a diffusion scrubber and a chromatograph.
Figure 2:
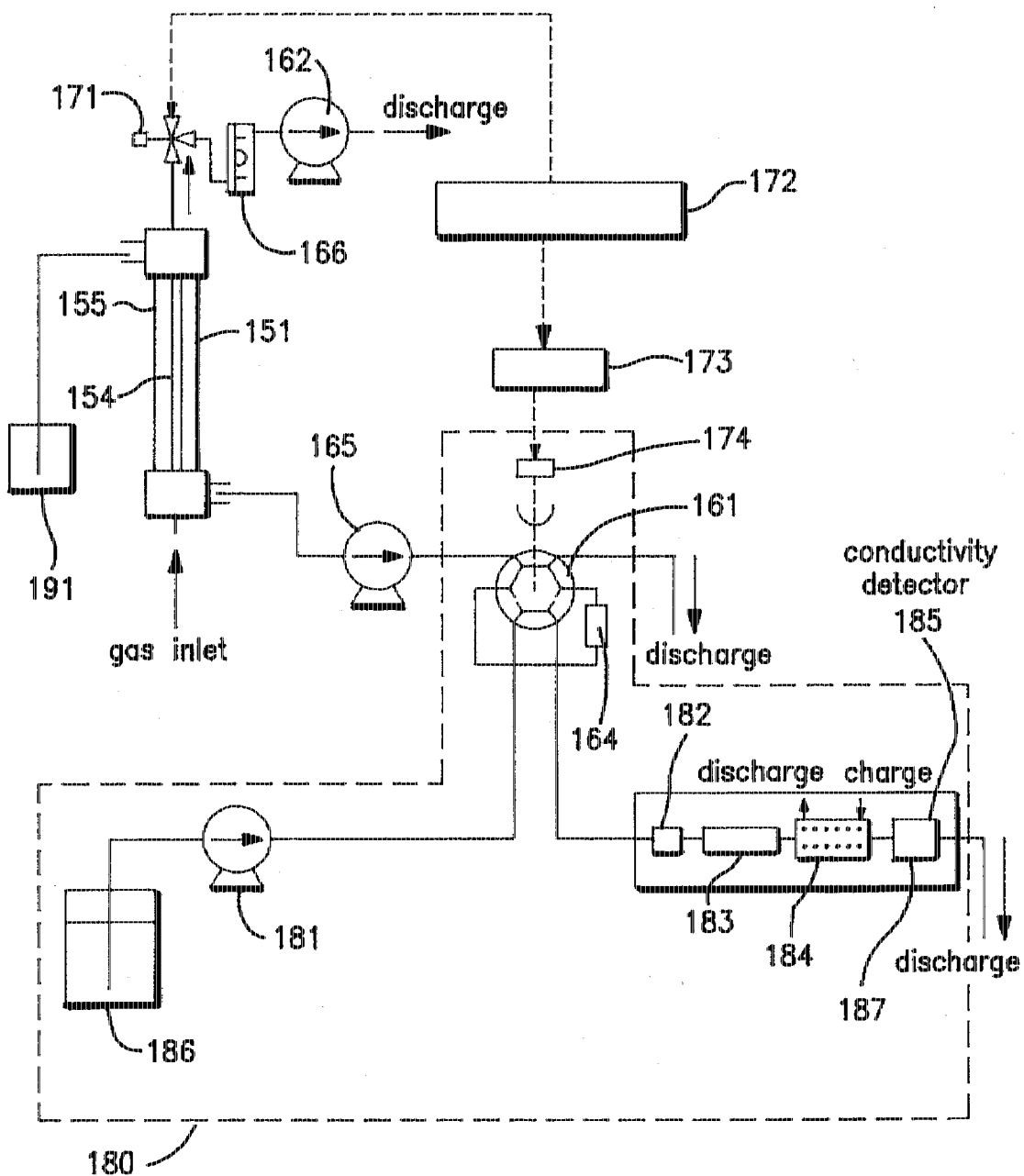
FIG. 2 is a diagram illustrative of the other conventional gas component analyzing system having a diffusion scrubber and a chromatograph.

The invention provides an apparatus for collecting gas components in which there is provided a diffusion scrubber comprising an inner tube and an outer tube, the inner tube comprising a gas penetrating membrane through which sampling gases only may penetrate, where sampling gases flow through inside of the inner tube and an absorption liquid flows through between the inner and outer tubes so that the absorption liquid absorbs the sampling gases penetrated through the membrane from the inside of the inner tube.

In the gas collection apparatus, there is further provided an absorption liquid feeding pump upstream from the diffusion scrubber for feeding the absorption liquid into between the inner and outer tubes of the diffusion scrubber.

There is further provided at least a flow passage switch valve downstream from of the diffusion scrubber, the flow passage switch valve having at last three way flow passages, each of which has a port, one of the ports being coupled to the diffusion scrubber.

There is further provided an absorption liquid reservoir coupled to other one of the ports than the one port coupled to the diffusion scrubber, the reverver reserving the absorption liquid for subsequent feeding of the absorption liquid through the flow passage switch valve.

There is further provided a circulation flow passage for the absorption liquid, the circulation flow passage connecting among the flow passage switch valve, the absorption liquid feeding pump and the diffusion scrubber.

There is further provided a non-circulation flow passage for the absorption liquid, the non-circulation flow passage connecting the absorption liquid reserver through the flow passage switch valve and the absorption liquid feeding pump into the diffusion scrubber.

The flow passage switch valve renders the current flow passage switch between the circulation and non-circulation flow passages.

The diffusion scrubber fixes the inner and outer tubes by a set of joint members provided at longitudinal opposite ends of the diffusion scrubber, an inlet port for the absorption liquid being provided at one of the opposite ends and an outlet port for the absorption liquid being provided at another of the opposite ends.

There may optionally be further provided a sample injection valve between upstream of the diffusion scrubber and downstream of The absorption liquid feeding pump, the sample injection valve comprising at least six way flow passages, each of which has a port, and a concentration column being provided to the sample injection valve through different ports from the ports used for coupling between the diffusion scrubber and the absorption liquid feeding pump.

The sample injection valve switches between different two flow passages, in one flow passage the concentration column is incorporated into the circulation or non-circulation flow passage, in another flow passage the concentration column is isolated from the circulation or non-circulation flow passage.

There may optionally be further provided a gas sampling pump at one end of the diffusion scrubber for feeding sampling gases into the diffusion scrubber.

The flow passage switch valve may have four way flow passages or three way flow passages.

In case of the three way flow passage, there may optionally be further provided a defoamer being provided at upstream of the flow passage switch valve for removing any foams in the absorption liquid, the defoamer having at least three ports, first one being used for import of the absorption liquid, second one being used for export of the absorption liquid and third one being used for export of the sampling gases, and a check valve being provided at the third port for restricting flow ways of the absorption liquid into one way. The absorption liquid reservoir may optionally be positioned at a higher level than a level of the defoamer which is positioned at a higher level than one end portion of a pipeline, opposite end of which is connected to a gas export of the defoamer so that there is fed from the absorption liquid reservoir into the defoamer a larger amount of the absorption liquid than an amount thereof fed by the absorption liquid pump due to siphon effect.

The absorption liquid reserver may have a cap and at least two connective ports, one port being for feeding the absorption liquid in the reserver into the non-circulation flow passage, another one being coupled a pipeline with a control valve for introducing air or an inert gas into the reservoir.

The present invention also provides an apparatus for analyzing gas components comprising one or more gas collectors and a gas analyzer.

In the gas collector, there is provided a diffusion scrubber comprising an inner tube and an outer tube, the inner tube comprising a gas penetrating membrane through which sampling gases only may penetrate, where sampling gases flow through inside of the inner tube and an absorption liquid flows through between the inner and outer tubes so that the absorption liquid absorbs the sampling gases penetrated through the membrane from the inside of the inner tube.

There is further provided an absorption liquid feeding pump upstream from the diffusion scrubber for feeding the absorption liquid into between the inner and outer tubes of the diffusion scrubber.

There is further provided at least a flow passage switch valve downstream from of the diffusion scrubber, the flow passage switch valve having at least three way flow passages, each of which has a port, one of the ports being coupled to the diffusion scrubber.

There is further provided an absorption liquid reservoir coupled to other one of the ports than one port coupled to the diffusion scrubber, the reservoir reserving the absorption liquid for subsequent feeding of the absorption liquid through the flow passage switch valve.

There is further provided a circulation flow passage for the absorption liquid, the circulation flow passage connecting among the flow passage switch valve, the absorption liquid feeding pump and the diffusion scrubber.

There is further provided a non-circulation flow passage for the absorption liquid, the non-circulation flow passage connecting the absorption liquid reservoir through the flow passage switch valve and the absorption liquid feeding pump into the diffusion scrubber.

There is further provided a sample injection valve between upstream of the diffusion scrubber and downstream of the absorption liquid feeding pump, the sample injection valve comprising at least six way flow passages, each of which has a port.

There is further provided a concentration column to the sample injection valve through different ports from the ports used for coupling between the diffusion scrubber and the absorption liquid feeding pump.

The flow passage switch valve renders the current flow passage switch between the circulation and non-circulation flow passages.

In the gas analyzer, there is provided an eluate reservoir for reserving an eluate to be used for eluting sampling gas components for subsequent analysis thereof.

There is further provided an eluate pump between the sample injection valve and the eluate reservoir for feeding the elute from the elute reservoir into the sample injection valve, the eluate pump being coupled to other port of the sample injection valve than the ports coupled to the diffusion scrubber and the concentration column respectively.

There is further provided a detector for detecting gas components eluted in the elution, the detector being coupled to the sample injection valve through a different port of the valve from the ports respectively coupled to the diffusion scrubber, the concentration column and the elution reservoir so as to form a gas analyzer flow passage connecting the eluate reservoir through the eluate pump and the sample injection valve into the detector.

The sample injection valve switches between different two flow passages, in one flow passage the concentration column is incorporated into an absorption liquid flow passage system, in another flow passage the concentration column is separated from the absorption liquid flow passage system.

The detector may comprise a liquid chromatograph or an ion chromatograph.

The diffusion scrubber fixes the inner and outer tubes by a set of joint members provided at longitudinally opposite ends of the diffusion scrubber, an inlet port for the absorption liquid being provided at one of the opposite ends and an outlet port for the absorption liquid being provided at another of the opposite ends.

There may optionally be further provided a sample injection valve between upstream of the diffusion scrubber and downstream of the absorption liquid feeding pump, the sample injection valve comprising at least six way flow passages, each of which has a port.

There may optionally be further provided a concentration column to the sample injection valve through different ports from the ports used for coupling between the diffusion scrubber and the absorption liquid feeding pump.

The sample injection valve switches between different two flow passages, in one flow passage the concentration column is incorporated into the circulation or non-circulation flow passage, in another flow passage the concentration column is isolated from the circulation or non-circulation flow passage.

There may optionally be further provided a gas sampling pump at one end of the diffusion scrubber for feeding sampling gases into the diffusion scrubber.

The flow passage switch valve may have four way flow passages or three way flow passages.

There may optionally be further provided a defoamer at upstream of the flow passage switch valve for removing any foams in the absorption liquid, the defoamer having at least three ports, first one being used for import of the absorption liquid, second one being used for export of the absorption liquid and third one being used for export of the sampling gases.

There may optionally be further provided a check valve at the third port for restricting flow ways of the absorption liquid into one way.

The absorption liquid reserver may optionally be positioned at a higher level than a level of the defoamer which is positioned at a higher level than one end portion of a pipeline, opposite end of which is connected to a gas export of the defoamer so that there is fed from the absorption liquid reservoir into the defoamer a larger amount of the absorption liquid than an amount thereof fed by the absorption liquid pump.

The absorption liquid reserver may have a cap and at least two connective ports, one port being for feeding the absorption liquid in the reservoir into the non-circulation flow passage, another one being coupled a pipeline with a control valve for introducing an air or an inert gas into the reservoir.

There may optionally be further provided a central control system coupled to the absorption liquid feeding pump for controlling operations of the absorption liquid feeding pump, the central control system being also coupled to the elute pump for controlling operations of the eluate pump, the central control system being also coupled to the flow passage switch valve for controlling operations of the flow passage switch valve, the central control system being also coupled to the sample injection valve for controlling operations of the sample injection valve and the central control system being also coupled to the detector for fetching detected data about sampling gas components from the detector and subsequent data processing.

There may optionally be further provided a plurality of the gas collectors and wherein the sample injection valves of the gas collectors are connected in series between the eluate pump and the detector.

There may optionally be further provided a rinse water injection valve provided between the eluate pump and the sample injection valve, the rinsing water valve having six way flow passages.

There may optionally be further provided a rinse water measuring tube coupled to the rinse water injection valve through its ports other than ports coupled respectively to the eluate pump and to the sample injection valve, the rinse water measuring tube capable of measuring an amount of a rinse water by reserving the rinse water therein.

There may optionally be further provided a rinse water feeder coupled to the rinse water injection valve through its port other than the ports coupled respectively to the eluate pump, to the sample injection valve and to the rinse water measuring tube, the rinse water feeder feeding the rinse water to the rinse water injection valve.

The rinse water injection valve switches between different two flow passages, one flow passage allowing the rinse water fed from the rinse water feeder to be charged in the rinse water measuring tube, another flow passage allowing the rinse water charged in the rinse water measuring tube to be fed to the sample injection valve.

Alternatively, there may optionally be further provided a rinse water injection coupled between the eluate pump and the sample injection valve, the rinse water injection valve being being coupled between the diffusion scrubber and the sample injection valve, the rinsing water valve having six way flow passages.

There may optionally be further provided a rinse water measuring tube coupled to the rinse water injection valve through its ports other than ports coupled respectively to the elute pump and the sample injection valve and the diffusion scrubber, the rinse water measuring tube being capable of measuring an amount of a rinse water by reserving the rinse water therein.

There may optionally be further provided a rinse water feeder coupled to the rinse water injection valve through its port other than the ports coupled respectively to the elute pump, to the sample injection valve and to the rinse water measuring tube, the rinse water feeder feeding the rinse water to the rinse water injection valve.

The rinse water injection valve switches between different two flow passages, one flow passage allowing the rinse water fed from the rinse water feeder to be charged in the rinse water measuring tube, another flow passage allowing the rinse water charged in the rinse water measuring tube to be fed to the sample injection valve.

Alternatively, there may optionally be further provided a rinse water injection valve coupled between the sample injection valve and an absorption liquid import of the diffusion scrubber, the rinse water injection valve being also coupled between the flow passage switch valve and an absorption liquid export of the diffusion scrubber, the rinse water injection valve having a discharge port from which the rinse water is discharged.

The rinse water injection valve switches between two different flow passages, one flow passage both connecting the sample injection valve to the discharge port and connecting the absorption liquid import to the absorption liquid export, the another flow passage both connecting the sample injection valve to the absorption liquid imports and connecting the absorption liquid export to the flow passage switch valve.

The present invention provides a method for analyzing gas components by use of the above described gas component analyzing apparatus. The novel method comprises a previous step, a sampling step and an analyzing step.

In the previous step, the flow passage switch valve is switched into one flow passage state in which there is formed a non-circulation flow passage for the absorption liquid, the non-circulation flow passage connecting the absorption liquid reservoir through the flow passage switch valve and the absorption liquid feeding pump into the the diffusion scrubber.

Also, the sample injection valve is switched into a flow passage state in which the concentration column is incorporated into an eluate flow passage system.

Further, the absorption liquid reserved in the absorption liquid reserver through the absorption liquid pump is fed into an absorption liquid import of the diffusion scrubber and also sample gases are fed into the diffusion scrubber so that the above two feeding steps are kept to allow sample gas components to be captured into the absorption liquid at least until the gas components to be analyzed come into an equilibrium state between the absorption liquid and the sample gases.

In the sampling step, the flow passage switch valve is switched into a circulation flow passage connecting among the flow passage switch valve, the absorption liquid feeding pump and the the diffusion scrubber.

Also, the sample injection valve is switched into another flow passage state in which the concentration column is incorporated into an absorption liquid flow passage system.

Further, the absorption liquid, in which the sample gas components have been captured, is fed to the concentration column.

In the analyzing step, the flow passage switch valve is switched into the one flow passage state in which there is formed the non-circulation flow passage for the absorption liquid, the non-circulation flow passage connecting the absorption liquid reservoir through the flow passage switch valve and the absorption liquid feeding pump into the diffusion scrubber.

Also the sample injection valve is fed into the flow passage state in which the concentration column is incorporated into the eluate flow passage system so that the sampling gas components are eluted into the eluate.

Further, the eluate is fed into which the sample gas components have been eluted to the detector for detecting the sample gas components.

The previous, sampling and analyzing steps may optionally be carried out at least a plurality of times, wherein during the analyzing step carried out in the eluate flow passage, the previous step for the next time is carried out in the absorption liquid flow passage.

After repeating a predetermined number of sets of the previous, sampling and analyzing steps, an air or an inert gas may be fed to the absorption liquid to force airs to discharge from the absorption liquid feeding pump and from the defoamer.

In case of providing a plurality of the gas collectors, the plural gas collectors may carry out the previous and sampling steps with a time difference one another so that the gas analyzer carry out sequentially the analyzing steps with respect to the plural gas collectors.

The present invention also provides a method for analyzing gas components by use of a gas analyzer system comprising one or more gas collectors and a gas analyzer. The method comprises a previous step, a rinsing step, a sampling step and an analyzing step.

In the previous step, the flow passage switch valve is switched into one flow passage state in which there is formed a non-circulation flow passage for the absorption liquid, the non-circulation flow passage connecting the absorption liquid reservoir through the flow passage switch valve and the absorption liquid feeding pump into the diffusion scrubber.

Also, the sample injection valve is fed into a flow passage state in which the concentration column is incorporated into an eluate flow passage system.

Also, the rinse water injection valve is switched into one flow passage allowing the rinse water fed from the rinse water feeder to be charged in the rinse water measuring tube.

Further, the absorption liquid reserved in the absorption liquid reservoir through the absorption liquid pump is fed into an absorption liquid import of the diffusion scrubber and also the sample gases are fed into the diffusion scrubber so that the above two feeding steps are kept to allow sample gas components to be captured into the absorption liquid at least until the gas components to be analyzed come into an equilibrium state between the absorption liquid and the sample gases.

In the rinsing step, the rinse water injection valve is switched into another flow passage allowing the rinse water charged in the rinse water measuring tube to be fed through the eluated flow passage system and then the sample injection valve into the concentration column to thereby wash the eluate out from the concentration column.

In the sampling step, the flow passage switch valve is switched into a circulation flow passage connecting among the flow passage switch valve, the absorption liquid feeding pump and the diffusion scrubber.

Also the sample injection valve is switched into another flow passage state in which the concentration column is incorporated into an absorption liquid flow passage system.

Further, the absorption liquid in which the sample gas components have been captured is fed to the concentration column.

In the analyzing step, the flow passage switch valve is switched into the one flow passage state in which there is formed the non-circulation flow passage for the absorption liquid, the non-circulation flow passage connecting the absorption liquid reservoir through the flow passage switch valve and the absorption liquid feeding pump into the diffusion scrubber.

Also the rinse water injection valve is switched into one flow passage allowing the rinse water fed from the rinse water feeder to be charged in the rinse water measuring tube.

Also the sample injection valve is switched into the flow passage state in which the concentration column is incorporated into the eluate flow passage system so that the sampling gas components are eluted into the eluate.

Further, the eluate into which the sample gas components have been eluted is fed to the detector for detecting the sample gas components.

The previous, sampling and analyzing steps are carried out at least a plurality of times, wherein during the analyzing step carried out in the eluate flow passage, the previous step for the next time is carried out in the absorption liquid flow passage.

After repeating a predetermined number of sets of the previous, sampling and analyzing steps, an air or an inert gas is fed to the absorption liquid to force airs to discharge from the absorption liquid feeding pump and from the defoamer.

In case of providing a plurality of the gas collectors, the plural gas collectors may carry out the previous and sampling steps with a time difference from one another so that the gas analyzer can carry out sequentially the analyzing steps with respect to the plural gas collectors.

The present invention provides a method for analyzing gas components by use of a gas analyzer system comprising one or more gas collectors and a gas analyzer. The method comprises a previous step, a rinsing step, a sampling step and an analyzing step.

In the previous step, the flow passage switch valve is switched into one flow passage state in which there is formed a non-circulation flow passage for the absorption liquid, the non-circulation flow passage connecting the absorption liquid reserver through the flow passage switch valve and the absorption liquid feeding pump into the diffusion scrubber.

Also the sample injection valve is switched into a flow passage state in which the concentration column is incorporated into an eluate flow passage system.

Also the rinse water injection valve is switched into one flow passage allowing the rinse water fed from the rinse water feeder to be charged in the rinse water measuring tube.

Further, the absorption liquid reserved in the absorption liquid reserver through the absorption liquid pump is fed into an absorption liquid import of the diffusion scrubber and the sample gases are fed into the diffusion scrubber so that the above two feeding steps are kept to allow sample gas components to be captured into the absorption liquid at least until the gas components to be analyzed come into an equilibrium state between the absorption liquid and the sample gases.

In the rinsing step, the rinse water injection valve is switched into another flow passage allowing the rinse water charged in the rinse water measuring tube to be fed through the eluate flow passage system and then the sample injection valve into the concentration column to thereby wash the eluate out from the concentration column.

In the sampling step, the flow passage switch valve is switched into a circulation flow passage connecting among the flow passage switch valve, the absorption liquid feeding pump and the the diffusion scrubber.

Also the sample injection valve is fed into another flow passage state in which the concentration column is incorporated into an absorption liquid flow passage system.

Further, the absorption liquid in which the sample gas components have been captured is fed to the concentration column.

In the analyzing step, the flow passage switch valve is switched into the one flow passage state in which there is formed the non-circulation flow passage for the absorption liquid, the non-circulation flow passage connecting the absorption liquid reserver through the flow passage switch valve and the absorption liquid feeding pump into the the diffusion scrubber.

Also, the rinse water injection valve is switched into one flow passage allowing the rinse water fed from the rinse water feeder to be charged in the rinse water measuring tube.

Also, the sample injection valve is switched into the flow passage state in which the concentration column is incorporated into the eluate flow passage system so that the sampling gas components are eluted into the eluate.

Further, the eluate into which the sample gas components have been eluted is fed to the detector for detecting the sample gas components.

The previous, sampling and analyzing steps may be carried out at least a plurality of times, wherein during the analyzing step carried out in the elute flow passage, the previous step for the next time is carried out in the absorption liquid flow passage.

After repeating a predetermined number of sets of the previous, sampling and analyzing steps, an air or an inert gas may be fed to the absorption liquid to force air to discharge from the absorption liquid feeding pump and from the defoamer.

In case of providing a plurality of the gas collectors, the plural gas collectors may carry out the previous and sampling steps with a time difference one another so that the gas analyzer carry out sequentially the analyzing steps with respect to the plural gas collectors.

The present invention also provides a method for analyzing gas components by use of a gas analyzer system comprising one or more gas collectors and a gas analyzer. The method comprises a previous step, a rinsing step, a sampling step and an analyzing step.

In the previous step, the flow passage switch valve is switched into one flow passage state in which there is formed a non-circulation flow passage for the absorption liquid, the non-circulation flow passage connecting the absorption liquid reserver through the flow passage switch valve and the absorption liquid feeding pump into the the diffusion scrubber.

Also, the sample injection valve is switched into a flow passage state in which the concentration column is incorporated into an eluate flow passage system.

Also, the rinse water injection valve is switched into one flow passage state in which the sample injection valve is connected to the absorption liquid import and the absorption liquid export is connected to the flow passage switch valve.

Further, the absorption liquid reserved in the absorption liquid reservoir through the absorption liquid pump is fed into an absorption liquid inlet of the diffusion scrubber and the sample gases are fed into the diffusion scrubber so that the two feeding steps are kept to allow sample gas components to be captured into the absorption liquid at least until the gas components to be analyzed come into an equilibrium state between the absorption liquid and the sample gases.

In the rinsing step, the rinse water injection valve is switched into another flow passage state in which the sample injection valve is connected to the discharge port and the absorption liquid import is connected to the absorption liquid export so that the absorption liquid washes the eluate out from the concentration column.

In the sampling step, the flow passage switch valve is switched into a circulation flow passage connecting among the flow passage switch valve, the absorption liquid feeding pump and the the diffusion scrubber.

Also, the rinse water injection valve is switched into one flow passage state in which the sample injection valve is connected to the absorption liquid import and the absorption liquid export is connected to the flow passage switch valve.

Also, the sample injection valve is switched into another flow passage state in which the concentration column is incorporated into an absorption liquid flow passage system.

Further, the absorption liquid in which the sample gas components have been captured is fed to the concentration column.

In the analyzing step, the flow passage switch valve is switched into the one flow passage state in which there is formed the non-circulation flow passage for the absorption liquid, the non-circulation flow passage connecting the absorption liquid reserver through the flow passage switch valve and the absorption liquid feeding pump into the diffusion scrubber.

Also the rinse water injection valve is switched into the one flow passage state in which the sample injection valve is connected to the absorption liquid import and the absorption liquid export is connected to the flow passage switch valve.

Also, the sample injection valve is switched into the one flow passage state in which the concentration column is incorporated into the eluate flow passage system.

Further, the eluate into which the sample gas components have been eluted is fed to the detector for detecting the sample gas components.

After the previous step, the rinsing, sampling and analyzing steps are repeated in turn.

The previous, sampling and analyzing steps are carried out at least a plurality of times, wherein during the analyzing step carried out in the eluate flow passage, the previous step for the next time is carried out in the absorption liquid flow passage.

After repeating a predetermined number of sets of the previous, sampling and analyzing steps, an air or an inert gas is fed to the absorption liquid to force air to discharge from the absorption liquid feeding pump and from the defoamer.

In case of providing a plurality of the gas collectors, the plural gas collectors carry out the previous and sampling steps with a time difference one another so that the gas analyzer carry out sequentially the analyzing steps with respect to the plural gas collectors.

Prior to the description as to preferred embodiments, operation of the apparatus for analyzing the gas components will generally be described.

According to the present invention, the absorption liquid flow passage for feeding the absorption liquid to the diffusion scrubber may be switched between the circulation and non-circulation state by controlling the flow passage switch valve. Switching the sample injection valve may select either the sampling flow passage for feeding the absorption liquid to the concentration column for concentration of the gas components intended to be analyzed or the analyzing flow passage for feeding the eluate to the concentration column in case of an intended elution or the concentrated gas component for subsequent detection of the gas component.

In the diffusion scrubber, the absorption liquid passes through between the inner and outer tubes, while the sample gases pass through the inside of the inner tube so that the gas components may penetrate through the micro-porous and be absorbed into the absorption liquid. Immediately after the sampling gases comes to pass through the diffusion scrubber, the gas component has not yet come to the required equilibrium state between the sampling gases and the absorption liquid. For that reason, the present invention provides the previous process to the sampling process.

In the previous process, the flow passage switch valve is switched to form the non-circulation flow passage so that a fresh absorption liquid is fed from the reservoir to the diffusion scrubber for a necessary time for allowing the gas component to take the required equilibrium state between the sampling gases and the absorption liquid.

After the required equilibrium state was obtained in the previous process, the flow passage switch valve and the sample injection valve are switched to form the circulation flow passage and the sampling flow passage to commence the intended sampling process. The absorption liquid having already captured the gas component in the diffusion scrubber is fed to the concentration column where the gas component is absorbed to the absorbent therein, resulting in the gas component showing the intended concentration.

Contrary to the present invention, if the absorption liquid is fed at a flow rate of 1 ml/min. on the non-circulation flow passage for ten minutes sampling 10 ml of an impurity included in the absorption liquid provides the no-load running text value.

By contrast, according to the present invention, the circulation flow passage is used for sampling the gas component thereby, under a condition for a flow passage capacity not more than 5 ml, a no-load running test valve being half of or less than that value when using the non-circulation flow passage. The no-load running test vale doe to the impurity in the absorption liquid is constant independently from the sampling time. Rendering the sampling time longer may provide an improvement in the S/B vale thereby allowing the minimum detectable vale to be lowered.

After the sampling process, the flow passage switch valve is switched to form the non-circulation flow passage and the sample injection valve is switched to form the analyzing flow passage so as to feed the eluate reserved in the eluate reservoir to the concentration column where the concentrated gas component show an elution for subsequent transmission thereof into the detector for detecting the gas component. During this term, the non-circulation flow passage for the absorption liquid serves to conduct the next time previous process.

In the diffusion scrubber, the absorption liquid is made contact with the sampling gases to absorb the gas components not only one intended to be analyzed but also other one. A part of the absorbed gases in the absorption liquid may show foams which may cause trouble in the pump, but the foams generated are removed by the defoamer provided on the absorption liquid flow passage. The air captured by the defoamer is discharged through the discharge port of the defoamer in the previous process.

For every predetermined number of process cycles, an air feeding control valve coupled to the absorption liquid reservoir is opened to feed an air or an inert gas to provide an air pressure for forcibly feeding the absorption liquid to remove any foam in the pump. Accordingly, the apparatus of the present invention is able to show a maintenance free successive operation for a long time.

There may be provided a control unit for central control of all the valves and the pumps so that automated operation of the apparatus is possible.

In the concentration column, not only the absorption liquid but also the eluate are introduced, for which reason there is a possibility that a remaining part of the eluate in the concentration column being fed to the absorption liquid flow passage together with the absorption liquid. The eluate mixed in the absorption liquid may prevent the required absorption and concentration of the gas component in the concentration column, resulting in a reduction of the collection efficiency. To settle this problem, there may optionally be provided a rinsing process for rinsing any remaining parts of the elution out from the concentration column for subsequent introduction of the absorption liquid thereinto.

The rinsing water flow passage valve may be provided just downstream from the eluate pump to introduce the rinse water into the eluate, or in place the rinsing water flow passage valve may be coupled to the absorption liquid flow passage.

A three way valve is provided between the sample injection valve and the inlet port of the diffusion scrubber so that in the rinsing process the absorption liquid is introduced into the concentration column and then discharged without introduction thereof into the diffusion scrubber for washing the eluate out.

During the rinsing process, it may be possible to introduce the atmosphere into the diffusion scrubber so that the gas components are introduced into the concentration column in the subsequent sampling process.

PREFERRED EMBODIMENTS OF THE INVENTION

Figure 4:
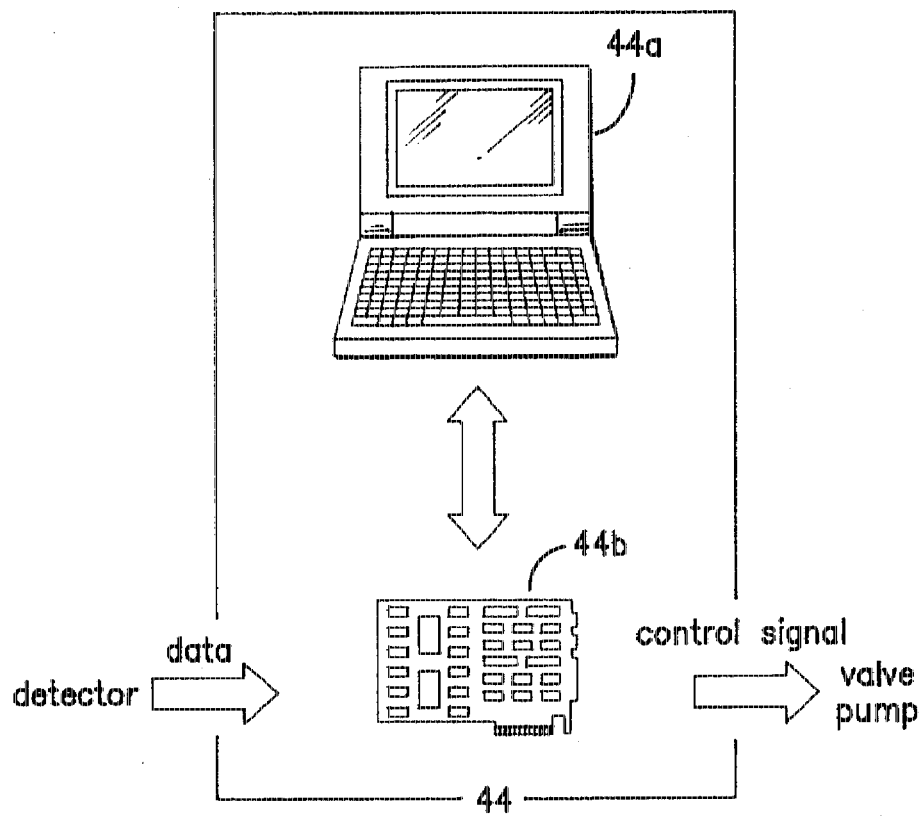
FIG. 4 is a view illustrative of a control unit involved in a novel gas component analyzing system having a diffusion scrubber and a chromatograph according to the present invention.
Figure 5:
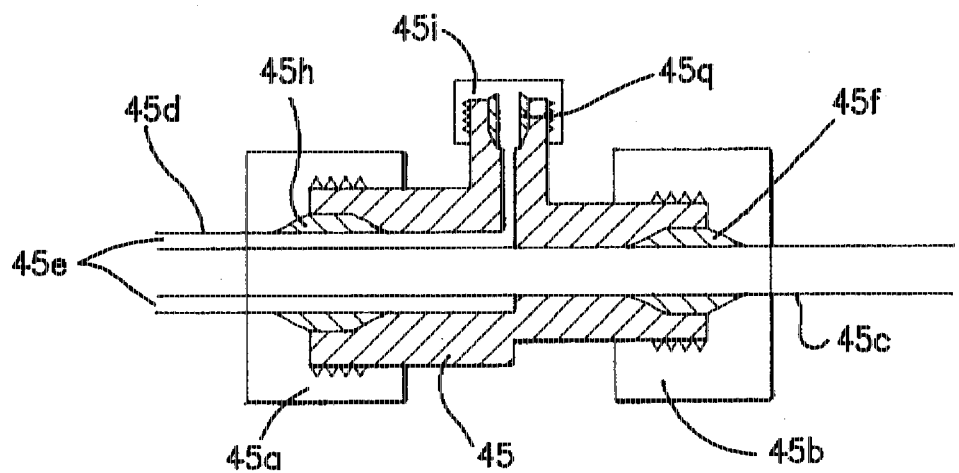
FIG. 5 is a cross sectional elevation view illustrative of a joint mechanism between inner and outer tubes of a diffusion scrubber involved in a novel gas component analyzing system with a chromatograph according to the present invention.

A first embodiment according to the present invention will be described in detail with reference to FIGS. 3, 4 and 5 in which there is provided a novel gas component analyzing system having a diffusion scrubber and an ion chromatograph.

Figure 3:
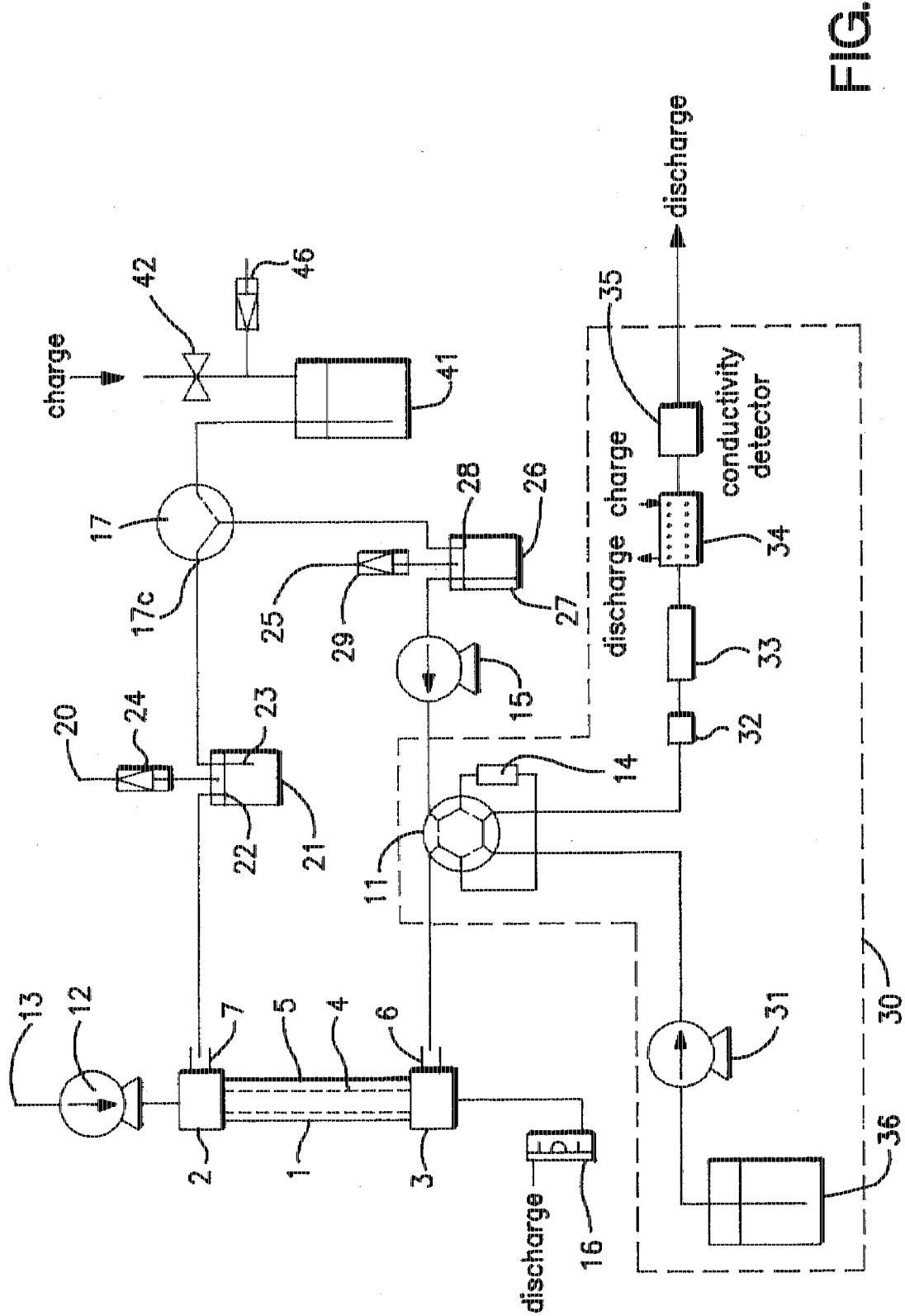
FIG. 3 is a diagram illustrative of a novel gas component analyzing system having a diffusion scrubber and a chromatograph in first and second embodiments according to the present invention.

As illustrated in FIG. 3, the novel gas component analyzing system comprises a gas collection system and an ion chromatograph 30 for analyzing an ammonia component in an atmosphere. The gas collection system includes a diffusion scrubber 1. The diffusion scrubber further comprises an inner tube 4 and an outer tube 5. The inner tube 4 comprises a microporous fluororesin membrane tube (Porflon tube TB-32) having a length of 50 cm and being provided at its opposite ends with fluororesin tubes. The micro-porous fluororesin membrane tube allows gases to penetrate through the micro-porous, but prevent any liquid from penetrating through the same. The outer tube 5 comprises a fluororesin tube having a length of 70 cm and inner and outer diameters of 4 mm and 6 mm respectively. The inner and outer tubes 4 and 5 are fixed one another through joint members 2 and 3 provided at longitudinally opposite ends of the both tubes. Structures of the joint members 2 and 3 are illustrated in FIG. 5. The joint member 45 binds the outer and inner tube by receiving fastening with hollow nuts 45a and 45b. Teflon seals 45f and 45h are provided at longitudinally opposite ends of the joint member 45 for sealing between the joint member 45 and the inner or outer tube. At the inlet or outlet port, the joint member is fastened by a hollow nut 45i. A Teflon seal 45g is also provided at the end of the inlet or outlet port.

Sampling gases pass through the inside of the inner tube 4, while an absorption liquid for absorbing the sampling gases may pas through the outside of the inner tube 4 and the inside of the outer tube 5 so that sampling gas components passing through the inside of the inner tube 4 may penetrate through the micro-porous of the inner tube 4 into the outside of the inner tube 4 and inside of the outer tube 5 where the gas components are absorbed into the absorption liquid. The joint member 2 is provided with a gas inlet port and an absorption liquid outlet port 7. The joint member 3 is provided with a gas outlet port and an absorption liquid inlet port 6.

The diffusion scrubber 1 is coupled through its gas inlet port to a sampling gas pump 12 which is further coupled to a gas inlet port 13 so that sampling gases are fed through the sampling gas pump 12 into the inside of the inner tube 4. The gases are fed to a flow meter 16 and then discharged.

The diffusion scrubber 1 is coupled through its absorption liquid inlet port to a sample injection valve 11. The sample injection valve 11 has a six way passage and six connective ports. The six connective ports are named as first to sixth connective ports in a clockwise direction for convenience of the following description. The absorption liquid inlet port 6 of the diffusion scrubber 1 is coupled to a first connective port of the sample injection valve 11 which is provided with a concentration column (Ion Pac CG12) 14 through its third and sixth connective ports. In the concentration column 14, the gas components captured in the absorption liquid are then concentrated.

The sample injection valve 11 is also coupled to an absorption liquid pump 15 which is further coupled to a defoamer 26 for removing any foams in the absorption liquid. The defoamer 26 is provided with a discharge port 25 from which a part of the absorption liquid in the defoamer 26 is discharged together with air or foams in the liquid. The discharge port 25 is provided with a check valve 29. The defoamer 26 is coupled through its outlet pipe 27 to the absorption liquid pump 15 and also coupled through its inlet pipe 28 to a flow passage switch valve 17. The flow passage switch valve 17 has three way passages and three connective ports. The three connective ports are herein named as first to third ports. The flow passage switch valve 17 is coupled through the first port to the defoamer 26. The flow passage switch valve 17 is also coupled through the second port to another defoamer 21. The defoamer 21 has a discharge port 20 with a check valve 24 so that a part of the absorption liquid in the defoamer 21 is discharged together with airs or foams in the liquid from the discharge port 20. The defoamer also has an inlet pipe 22 coupled to the inlet port 7 of the diffusion scrubber 1 and an outlet pipe 23 connected to the second port of the flow passage switching valve 17. The flow passage switching valve 17 is coupled through its third port to an absorption liquid reserver 41 in which an absorption liquid is reserved. In this embodiment, the absorption liquid is a super pure water.

The flow passage switch valve 17 comes to take a first state in which the flow passage is formed between the first and second ports so that the first and second ports are connected one another. In this first state, there is formed a circulation absorption liquid flow passage. The flow passage switch valve 17 comes to take a second state in which the flow passage is formed between the first and third ports so that the first and third ports are connected to one another. In this second state, there is formed a non-circulation absorption liquid flow passage.

The ion chromatograph (DX100) 30 includes a series of a guard column (Ion Pac CG12) 32, a separation column (Ion Pac CS12) 33 coupled to the guard column 32, a suppresser (CSRS-I) 34 coupled to the separation column 33 and the electrical conductivity detector 35 coupled to the suppresser 34. The guard column 32 is connected to the fourth port of the sample injection valve 11. In the circulation absorption liquid flow passage, the sample injection valve 11 has a flow passage connecting between the fourth and fifth ports. The fifth port of the sample injection valve 11 is coupled to an eluate pump 31 which is further coupled to an eluate reservoir 36 in which 20 mM of methylsulfonic acid as the eluate is reserved.

Moreover, there is provided a control unit 44 including a computer 44a and an interface 44b connected to the computer 44a. Detection data detected by the detector in the ion chromatograph are fetched and inputted through the interface 44b into the computer 44a for subsequent generation of control signals to be transmitted to individual valves and pumps for controlling motions thereof as illustrated in FIG. 4.

The flow passage for the absorption liquid switches between the circulation flow passage and the non-circulation flow passage. The flow passage for the elute switches between the analyzing flow passage and non-analyzing flow passage.

The following descriptions will focus on the operations of the above described gas component analyzing system. The flow passage switch valve is switched to have the absorption liquid flow passage come into the non-circulation passage. Further, the sample injection valve is switched to have the elute flow passage come into the non-analyzing flow passage. A valve 42 is set open. The absorption liquid pump 15 is placed into an operation. Further, the ion chromatograph 30 is put in operation. The absorption liquid, for example, the super pure water is fed from the absorption liquid reserver 41 through the defoamer 26 into the absorption liquid pump 15. In the defoamer 26, a part of the absorption liquid is discharged from the discharge port 25 together with the air in the defoamer 26 and the remaining absorption liquid is fed to the absorption liquid pump 15.

After discharge of the air from the defoamer 26, the valve 42 comes close, while the flow passage switch valve 17, the sample injection valve 11 and the absorption liquid pump 15 are still kept. Atmosphere is sucked by the sampling gas pump 12 to have the atmosphere pass through the inside of the inner tube 4 of the diffusion scrubber 1. An amount of the sucked in atmosphere is controlled by the flow meter 16 for fifteen minutes. The absorption liquid is introduced into the inlet port 6 of the diffusion scrubber 1 and then charged between the inner and outer tubes 4 and 5, resulting in an overflow of the absorption liquid and subsequent discharge thereof from the outlet port 7. The overflowed and discharged absorption liquid is fed to the defoamer 21. Since the second port of the flow passage switch valve is closed, the absorption liquid is discharged from the discharge port 20 together with an air in the defoamer 21. As a result, the defoamer 21 is filled with the absorption liquid. The absorption liquid between the outlet port 7 of the diffusion scrubber 1 and the defoamer 21 comes into an equilibrium state in ammonia to the sampling atmosphere passing through the diffusion scrubber 1. The above previous step is maintained for fifteen minutes.

The flow passage switch valve 17 and the sample injection valve 11 are switched to have the absorption liquid flow passage come into the circulation flow passage or the sampling flow passage so that the absorption liquid passes through the concentration column 14 thereby conducting a concentration of the analyzing gas components. This sampling process is continued for fifteen minutes. Since the absorption liquid flow passage have come into the circulation flow passage, the absorption liquid in the defoamer 21 is fed through the flow passage switch valve 17 to the defoamer 26. In the diffusion scrubber 1, the absorption liquid shows an absorption of gas components including at least ammonia. This absorption liquid is fed through the circulation flow passage into the concentration column 14 where ammonia component is absorbed into an absorbent of the concentration column and then concentrated. Then, the absorption liquid is circulated to the diffusion scrubber for absorption of the ammonia gas component. Since the absorption liquid is kept circulated during the sampling process, a no-load running test value is kept constant. This means that a long time sampling results in an improvement in S/B ratio thereby a detectable minimum valve is lowered.

The flow passage switch valve 17 is switched to have the absorption liquid flow passage come into the non-circulation flow passage. The sample injection valve 11 is switched to have the elute flow passage come into the analyzing flow passage. As a result, the eluate reserved in the eluate reservoir 36 is fed through the eluate pump 31 to the concentration column 14 where the eluate may cause an elution of the concentrated ammonia, which has been concentrated in the concentration column 14 in the sampling process. The eluted ammonia is then fed together with the eluate to the guard column 32 and then the separation column 33 where ammonia component is separated from other anion components. The ammonia component is then fed to the suppresser 34 where an electrical conductivity of background is reduced. The ammonia component is then fed to the electrical conductivity detector 35 for measurement of the electrical conductivity. A variation in conductivity versus time is inputted as data through the interface 44b into the computer 44a in the control unit 44 illustrated in FIG. 4. From the inputted data, the computer 44a sequentially conducts the required preparation of the chromatograph, a detection of peak with respect to ammonia, a computation of peak area, a computation of ammonia concentration in the sample atmosphere and output of resultant data via a screen or a printer.

Meanwhile, during the above analyzing process, on the non-circulation flow passage for the absorption liquid, the previous process is carried out as the next process.

The above analyzing process is continued for fifteen minutes, after which the flow passage switch valve 17 and the sample injection valve 11 are switched to form the circulation flow passage and the sampling flow passage. Subsequently, in accordance with the number of successive measurements predetermined by the computer 44a, the above sampling process and the analyzing process are alternatively carried out for plural measurements of ammonia in the atmosphere every thirty minutes.

A second embodiment according to the present invention will be described in detail with reference to FIG. 3 in which there is provided a novel gas component analyzing system having a diffusion scrubber and an ion chromatograph.

The system in the second embodiment is completely the same as that of the first embodiment in the structure and the operations thereof. To prevent duplicate descriptions, descriptions as to the structure and operations of the novel gas analyzing system will be omitted. The second embodiment is different from the first embodiment in analyzing acid components in the atmosphere The ion chromatograph comprises a guard column 32 (Ion Pac AG4A-SC), a separation column 33 (ion Pac AS4A-SC), a concentration column 14 (Ion Pac AG4A-SC) and a suppresser 34 (ASRS-I).

In the absorption liquid reserver 41, the super pure water is reserved as an absorption liquid as the first embodiment, but in the eluate reservoir 36, there is reserved as an eluate a solution including 4 mM of sodium carbonate and 1.5 mM of sodium hydrogen-carbonate.

Providing additionally the control unit 44 may allow that all the valves and the pumps are controlled by control signals outputted from the computer 44a through the interface 44b and also that informationnal data about a variation in the measured electrical conductivity versus time are inputted through the interface 44b into the computer 44a where the inputted informational data are processed to obtain separated chromatograms of $CL^-$, $NO_2^-$, $NO_3^-$, $SO_4^{2-}$ etc. In he control unit 44, the detection with respect to the peaks of individual components, the computation of the peak areas, the computation of the acid components in the sample atmosphere are carried out so that resulted generated by the computations are outputted through the screen and the printer.

As modifications of the first and second embodiments, in place of the ion chromatograph, there may be used as a detector a flow injecting analyzer and a liquid chromatograph as well as any analyzers available to be coupled thereto.

A third embodiment according to the present invention will be described in detail with reference to FIG. 6 in which there is provided a novel gas component analyzing system having a diffusion scrubber and an ion chromatograph.

Figure 6:
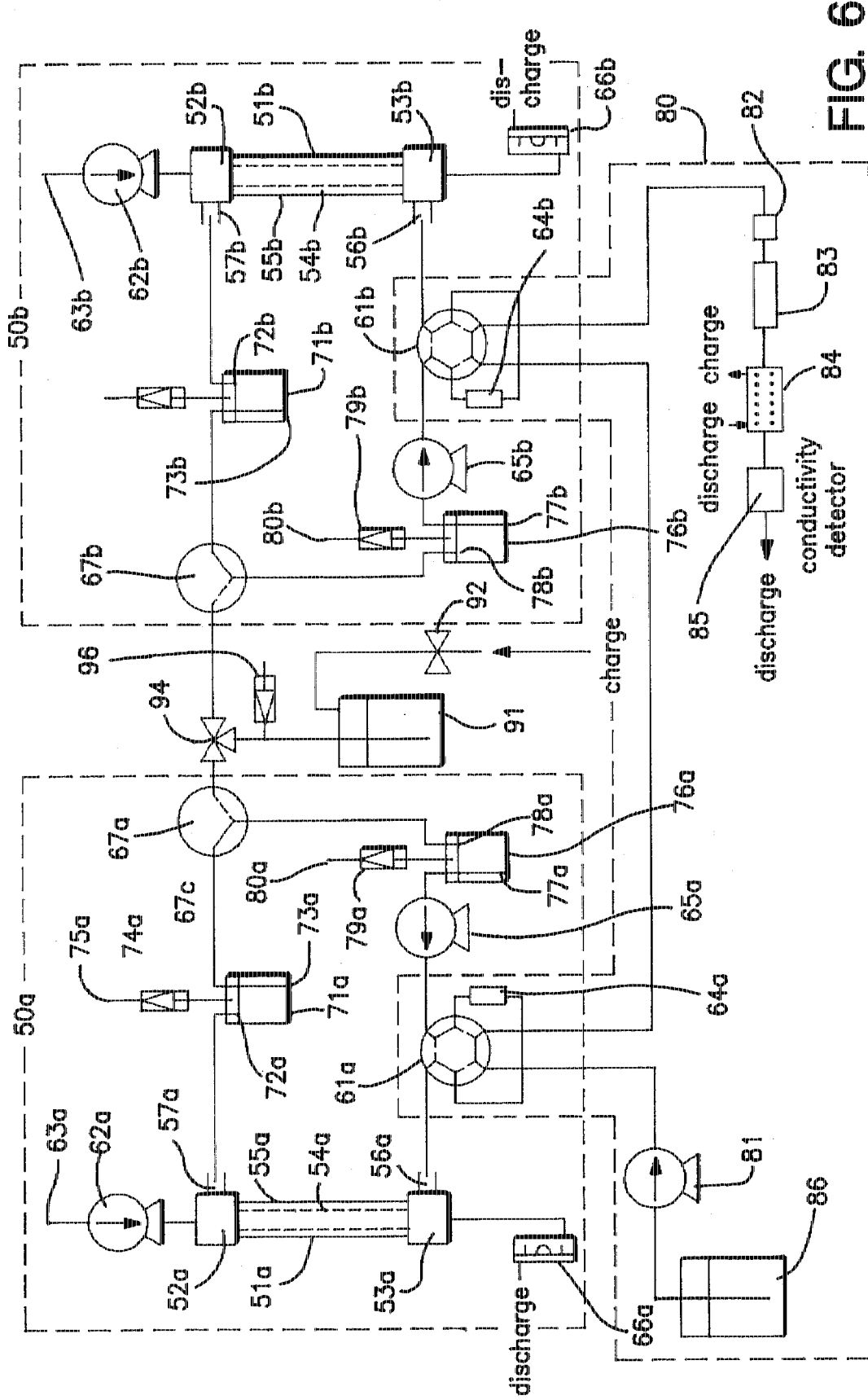
FIG. 6 is a diagram illustrative of a novel gas component analyzing system having a diffusion scrubber and a chromatograph in a third embodiment according to the present invention.

As illustrated in FIG. 6, the novel gas component analyzing system comprises two of first and second bas collection systems 50a and 50b and an ion chromatograph 50 for analyzing an ammonia component in an atmosphere. The first and second gas collection systems 50a and 50b have the same structure one another and the both are coupled to a single absorption liquid reservoir 91. through a three way valve 94 for receiving a supply of the absorption liquid.

The first gas collection system 50a includes a diffusion scrubber 51a. The diffusion scrubber 51a further comprises an inner tube 54a and an outer tube 55a. The inner tube 54a comprises a micro-porous fluororesin membrane tube (Porflon tube TB-32) having a length of 50 cm and being provided at its opposite ends with fluororesin tubes. The micro-porous fluororesin membrane tube allows gases to penetrate through the micro-porous, but prevent any liquid from penetrating through the same. The outer tube 55a comprises a fluororesin tube having a length of 70 cm and inner and outer diameters of 4 mm and 6 mm respectively. The inner and outer tubes 54a and 55a are fixed one another through joint members 52a and 53a provided at longitudinally opposite ends of the both tubes.

Sampling gases pass through the inside of the inner tube 54a, while an absorption liquid for absorbing the sampling gases may pass through the outside of the inner tube 54a and the inside of the outer tube 55a so that sampling gas components passing through the inside of the inner tube 54a may penetrate through the micro-porous of the inner tube 54a into the outside of the inner tube 54a and inside of the outer tube 55a where the gas components are absorbed into the absorption liquid. The joint member 52a is provided with a gas inlet port and an absorption liquid outlet port 57a. The joint member 53a is provided with a gas outlet port and an absorption liquid inlet port 56a.

The diffusion scrubber 51a is coupled through its gas inlet port to a sampling gas pump 62a which is further coupled to a gas inlet port 63a so that sampling gases are fed through the sampling gas pump 62a into the inside of the inner tube 54a. The gases are fed to a flow meter 66a and then discharged.

The diffusion scrubber 51a is also coupled through its absorption liquid inlet port 56a to a sample injection valve 61a. The sample injection valve 61a has six way passages and six connective ports. The six connective ports are named as first to sixth connective ports in a clockwise direction for convenience of the following description. The absorption liquid inlet port 56a of the diffusion scrubber 51a is coupled to a first connective port of the sample injection valve 61a which is provided with a concentration column (Ion Pac CG12) 64a through its third and sixth connective ports. In the concentration column 64a, the gas components captured in the absorption liquid is concentrated.

The sample injection valve 61a is also coupled to an absorption liquid pump 65a which is further coupled to a defoamer 76a for removing any foam from the absorption liquid. The defoamer 76a is provided with a discharge port 80a from which a part of the absorption liquid in the defoamer 76a is discharged together with air or foam in the liquid. The discharge port 80a is provided with a check valve 79a. The defoamer 76a is coupled through its outlet pipe 77a to the absorption liquid pump 65a and also coupled through its inlet pipe 78a to a flow passage switch valve 67a. The flow passage switch valve 67a has three way passages and three connective ports. The three connective ports are herein named as first to third ports. The flow passage switch valve 67a is coupled through the first port to the defoamer 76a. The flow passage switch valve 67a is also coupled through the second port to another defoamer 71a. The defoamer 71a has a discharge port 75a with a check valve 74a so that a part of the absorption liquid in the defoamer 71a is discharged together with airs or foam in the liquid from the discharge port 75a. The defoamer 71a also has an inlet pipe 72a coupled to the inlet port 57a of the diffusion scrubber 51a and an outlet pipe 73a connected to the second port of the flow passage switching valve 67a. The flow passage switching valve 67a is coupled through its third port to a commom absorption liquid reserver 91 commonly used by the counterpart gas collection system. In this embodiment, the absorption liquid is a super pure water.

The flow passage switch valve 67a comes to take a first state in which the flow passage is formed between the first and second ports so that the first and second ports are connected one another. In this first state, there is formed a circulation absorption liquid flow passage. The flow passage switch valve 67a comes to take a second state in which the flow passage is formed between the first and third ports so that the first and third ports are connected one another. In this second state, there is formed a non-circulation absorption liquid flow passage.

The first gas collection system 50b includes a diffusion scrubber 51b. The diffusion scrubber 51b further comprises an inner tube 54b and an outer tube 55b. The inner tube 54b comprises a micro-porous fluororesin membrane tube (Porflon tube TB-32) having a length of 50 cm and being provided at its opposite ends with fluororesin tubes. The micro-porous fluororesin membrane tube allows gases to penetrate through the micro-porous, but prevent any liquid from penetrating through the same. The outer tube 55b comprises a fluororesin tube having a length of 70 cm and inner and outer diameters of 4 mm and 6 mm respectively. The inner and outer tubes 54b and 55b are fixed one another through joint members 52b and 53b provided at longitudinally opposite ends of the both tubes.

Sampling gases pass through the inside of the inner tube 54a, while an absorption liquid for absorbing the sampling gases may pass through the outside of the inner tube 54b and the inside of the outer tube 55b so that sampling gas components passing through the inside of the inner tube 54b may penetrate through the micro-porous of the inner tube 54b into the outside of the inner tube 54b and inside of the outer tube 55b where the gas components are absorbed into the absorption liquid. The joint member 52b is provided with a gas inlet port and an absorption liquid outlet port 57b. The joint member 53b is provided with a gas outlet port and an absorption liquid inlet port 56b.

The diffusion scrubber 51b is coupled through its gas inlet port to a sampling gas pump 62b which is further coupled to a gas inlet port 63b so that sampling gases are fed through the sampling gas pump 62b into the inside of the inner tube 54b. The gases are fed to a flow meter 66b and then discharged.

The diffusion scrubber 51b is also coupled through its absorption liquid inlet port 56b to a sample injection valve 61b. The sample injection valve 61b has six way passages and six connective ports. The six connective ports are named as first to sixth connective ports in an anti-clockwise direction for convenience of the following description. The absorption liquid inlet port 56b of the diffusion scrubber 51b is coupled to a first connective port of the sample injection valve 61b which is provided with a concentration column (Ion Pac CG12) 64b through its third and sixth connective ports. In the concentration column 64a, the gas components captured in the absorption liquid are concentrated.

The sample injection valve 61b is also coupled to an absorption liquid pump 65b which is further coupled to a defoamer 76b for removing any foam from the absorption liquid. The defoamer 76b is provided with a discharge port 80b from which a part of the absorption liquid in the defoamer 76b is discharged together with air or foam in the liquid. The discharge port 80b is provided with a check valve 79b. The defoamer 76b is coupled through its outlet pipe 77b to the absorption liquid pump 65b and also coupled through its inlet pipe 78b to a flow passage switch valve 67b. The flow passage switch valve 67b has three way passages and three connective ports. The three connective ports are herein named as first to third ports. The flow passage switch valve 67b is coupled through the first port to the defoamer 76b. The flow passage switch valve 67b is also coupled through the second port to another defoamer 71b. The defoamer 71b has a discharge port 75b with a check valve 74b so that a part of the absorption liquid in the defoamer 71b is discharged together with air or foam in the liquid from the discharge port 75b. The defoamer 71b also has an inlet pipe 72b coupled to the inlet port 57b of the diffusion scrubber 51b and an outlet pipe 73b connected to the second port of the flow passage switching valve 67b. The flow passage switching valve 67b is coupled through its third port to a commom absorption liquid reservoir 91 commonly used by the counterpart gas collection system. In this embodiment, the absorption liquid is a super pure water.

The flow passage switch valve 67b comes to take a first state in which the flow passage is formed between the first and second ports so that the first and second ports are connected one another. In this first state, there is formed a circulation absorption liquid flow passage. The flow passage switch valve 67b comes to take a second state in which the flow passage is formed between the first and third ports so that the first and third ports are connected one another. In this second state, there is formed a non-circulation absorption liquid flow passage.

The ion chromatograph (DX100) 80 includes a series of a guard column (Ion Pac CG12) 82, a separation column (Ion Pac CS12) 83 coupled to the guard column 82, a suppresser (CSRS-I) 84 coupled to the separation column 83 and the electrical conductivity detector 85 coupled to the suppresser 84. The guard column 82 is connected to the fifth port of the sample injection valve 61b. In the state forming the circulation absorption liquid flow passage, the sample injection valve 61b has a flow passage connecting between the fourth and fifth ports. The fourth port of the sample injection valve 61b is coupled to the fourth port of the sample injection valve 61a. In the state forming the circulation absorption liquid flow passage, the sample injection valve 61a has a flow passage connecting between the fourth and fifth ports. The fifth port of the sample injection valve 61a is coupled to an eluate pump 81 which is further coupled to an eluate reservoir 86 in which 20 mM of methylsulfonic acid as the eluate is reserved.

With reference back to FIG. 6, there is provided a control unit 44 including a computer 44a and an interface 44b connected to the computer 44b. Detection data detected by the detector in the ion chromatograph 80 are fetched and inputted through the interface 44b into the computer 44a for subsequent generation of control signals to be transmitted to individual valves and pumps for controlling motions thereof.

The flow passage for the absorption liquid switches between the circulation flow passage and the non-circulation flow passage. The flow passage for the elute switches between the analyzing flow passage and non-analyzing and sampling flow passage.

The following descriptions will focus on the operations of the above described gas component analyzing system. The flow passage switch valves 67a and 67b are switched to have the first and third ports are connected one another so that the absorption liquid flow passages in the first and second gas collection system come into the non-circulation passage. Further, the sample injection valves 61a and 61b are switched to have the first and sixth ports connected one another and to have the second and third ports connected one another as well as to have the fourth and fifth ports connected one another. As a result, the elute flow passage come into the non-analyzing flow passage. A valve 92 is set open. The three way valve 94 is so set that three ports thereof are opened. The absorption liquid pumps 65a and 65b are placed into operation. Further, the ion chromatograph 80 is put in operation.

The absorption liquid, for example, the super pure water is fed from the absorption liquid reserver 91 through the defoamer 76a into the absorption liquid pump 65a. In the defoamer 76a, a part of the absorption liquid is discharged from the discharge port 80a together with the air in the defoamer 76a and the remaining absorption liquid is fed to the absorption liquid pump 65a.

Also, the absorption liquid, for example, the super pure water is fed from the absorption liquid reserver 91 through the defoamer 76b into the absorption liquid pump 65b. In the defoamer 76b, a part of the absorption liquid is discharged from the discharge port 80a together with the air in the defoamer 76b and the remaining absorption liquid is fed to the absorption liquid pump 65b.

After discharge of the air from each of the defoamers 76a and 76b, the valve 92 comes close, while there are still kept the three way valve 94, the flow passage switch valves 67a and 67b, the sample injection valves 61a and 61b and the absorption liquid pumps 65a and 65b. Atmospheres are suctioned by the sampling gas pumps 62a and 62b to have the atmospheres pass through the insides of the inner tube 54a and 54b of the diffusion scrubber 51a and 51b respectively. An amount of the suctioned atmosphere is controlled by each of the flow meters 66a and 66b.

In the gas collection system 50a, the absorption liquid is introduced into the inlet port 56a of the diffusion scrubber 51a and then charged between the inner and outer tubes 54a and 55a, resulting in an overflow of the absorption liquid and subsequent discharge thereof from the outlet port 57a. The overflowed and discharged absorption liquid is fed to the defoamer 71a. Since the second port of the flow passage switch valve 67a is closed, the absorption liquid is discharged from the discharge port 75a together with air in the defoamer 71a. As a result, the defoamer 71a is filled with the absorption liquid. The absorption liquid between the outlet port 77a of the diffusion scrubber 51a and the defoamer 71a comes into an equilibrium state in ammonia to the sampling atmosphere passing through the diffusion scrubber 51a.

In the gas collection system 50b, the absorption liquid is introduced into the inlet port 56b of the diffusion scrubber 51b and then charged between the inner and outer tubes 54b and 55b, resulting in an overflow of the absorption liquid and subsequent discharge thereof from the outlet port 57b. The overflowed and discharged absorption liquid is fed to the defoamer 71b. Since the second port of the flow passage switch valve 67b is closed, the absorption liquid is discharged from the discharge port 75b together with air in the defoamer 71b. As a result, the defoamer 71b is filled with the absorption liquid. The absorption liquid between the outlet port 77b of the diffusion scrubber 51b and the defoamer 71b comes into an equilibrium state in ammonia to the sampling atmosphere passing through the diffusion scrubber 51b.

The above previous process or step is completed fifteen minutes after the process is commenced. The next step is the sampling step. The sampling step is carried out by the first and second gas collection system with a time difference one another. The sampling step of the first gas collection system 50a precedes the sampling step of the second gas collection system 50b.

The flow passage switch valve 67a and the sample injection valve 61a are switched to have the absorption liquid flow passage come into the circulation flow passage or the sampling flow passage so that the absorption liquid passes through the concentration column 74a thereby conducting a concentration of the analyzing gas components. This sampling process is continued for fifteen minutes. Since the absorption liquid flow passage have come into the circulation flow passage, the absorption liquid in the defoamer 71a is fed through the flow passage switch valve 67a to the defoamer 76a. In the diffusion scrubber 51a, the absorption liquid shows an absorption of gas components including at least ammonia. This absorption liquid is fed through the circulation flow passage into the concentration column 64a where ammonia component is absorbed into an absorbent of the concentration column and then concentrated. Then, the absorption liquid is circulated to the diffusion scrubber for absorption of the ammonia gas component. Since the absorption liquid is kept circulated during the sampling process, a no-load running text value is kept constant. This means that a long time sampling results in an improvement in S/B ratio thereby a detectable minimum value is lowered.

Following to the sampling step of the first gas collection system 50a, the first gas collection system 50a will enter into the analyzing step, while the second gas collection 50b will enter into the sampling step.

In the first gas collection system 50a, the flow passage switch valve 67a is switched to have the absorption liquid flow passage come into the non-circulation flow passage. The sample injection valve 61a is switched to have the elute flow passage come into the analyzing flow passage. As a result, the eluate reserved in the eluate reservoir 86 is fed through the eluate pump 81 to the concentration column 64a where the eluate may cause an elution of the concentrated ammonia, which has been concentrated in the concentration column 64a in the sampling process. The eluted ammonia is then fed together with the eluate to the guard column 82 without passing through the concentration column 64b in the second gas collection system 50b. The eluted ammonia is then fed into the separation column 83 where ammonia component is separated from other anion components. The ammonia component is then fed to the suppresser 84 where an electrical conductivity of background is reduced. The ammonia component is then fed to the electrical conductivity detector 85 for measurement of the electrical conductivity. A variation in conductivity versus time is inputted as data through the interface 44b into the computer 44a in the control unit 44 illustrated in FIG. 4. From the inputted data, the computer 44a sequentially conducts the required preparation of the chromatograph, a detection of peak with respect to ammonia, a computation of peak area, a computation of ammonia concentration in the sample atmosphere and output of resultant data via a screen or a printer.

Meanwhile, during the above analyzing process of the first gas collection system 50a, the sampling process is carried out by the second gas collection system 50b. Further, the first gas collection system carries out the next previous process for the next time gas measurement process at the same time of the current analyzing process.

The flow passage switch valve 67b and the sample injection valve 61b are switched to have the absorption liquid flow passage come into the circulation flow passage or the sampling flow passage so that the absorption liquid passes through the concentration column 74b thereby conducting a concentration of the analyzing gas components. This sampling process is continued for fifteen minutes. Since the absorption liquid flow passage have come into the circulation flow passage, the absorption liquid in the defoamer 71b is fed through the flow passage switch valve 67b to the defoamer 76b. In the diffusion scrubber 51b, the absorption liquid shows an absorption of gas components including at least ammonia. This absorption liquid is fed through the circulation flow passage into the concentration column 64b where ammonia component is absorbed into an absorbent of the concentration column and then concentrated. Then, the absorption liquid is circulated to the diffusion scrubber for absorption of the ammonia gas component. Since the absorption liquid is kept circulated during the sampling process, a no-load running test value is kept constant. This means that a long time sampling results in an improvement in S/B ratio thereby a detectable minimum value is lowered.

The above processes are continued for fifteen minutes, after which the second gas collection system 50b will enter into the analyzing process, while the first gas collection system will enter into the sampling process for the next measurement.

In the Second gas collection system 50b, the flow passage switch valve 67b is switched to have the absorption liquid flow passage come into the non-circulation flow passage. The sample injection valve 61b is switched to have the elute flow passage come into the analyzing flow passage. As a result, the eluate reserved in the elute reserver 86 is fed through the eluate pump 81, without however passing through the concentration column 64a, to the concentration column 64b where the eluate may cause an elution of the concentrated ammonia, which has been concentrated in the concentration column 64b in the sampling process. The eluted ammonia is then fed together with the eluate to the guard column 82 without passing through the concentration column 64b in the second gas collection system 50b. The eluted ammonia is then fed into the separation column 83 where ammonia component is separated from other anion components. The ammonia component is then fed to the suppresser 84 where an electrical conductivity of background is reduced. The ammonia component is then fed to the electrical conductivity detector 85 for measurement of the electrical conductivity. A variation in conductivity versus time is inputted as data through the interface 44b into the computer 44a in the control unit 44 illustrated in FIG. 4. From the inputted data, the computer 44a sequentially conducts the required preparation of the chromatograph, a detection of peak with respect to ammonia, a computation of peak area, a computation of ammonia concentration in the sample atmosphere and output of resultant data via a screen or a printer.

Meanwhile, during the above analyzing process by the second gas collection system 50b, the next sampling process is carried out by the first gas collection system 50a for the next time gas component measurement. The second gas collection system also carries out the next previous process at the same time of the current analyzing process.

Subsequently, the first gas collection system enters into the analyzing process and the previous process, while the second gas collection system enters into the sampling process. The above processes by the first and second gas collection systems 50a and 50b are repeated a predetermined number of time.

Providing two of the gas collection systems 50a and 50b allows the ion chromatograph to conduct successive detections of the gas components without stopping of the operation.

As modifications of the first and second embodiments, in place of the ion chromatograph, there may be used as a detector a flow injecting analyzer and a liquid chromatograph as well as any analyzers available to be coupled thereto.

A fourth embodiment according to the present invention will be described in detail with reference to FIG. 7 in which there is provided a novel gas component analyzing system having a diffusion scrubber and an ion chromatograph.

Figure 7:
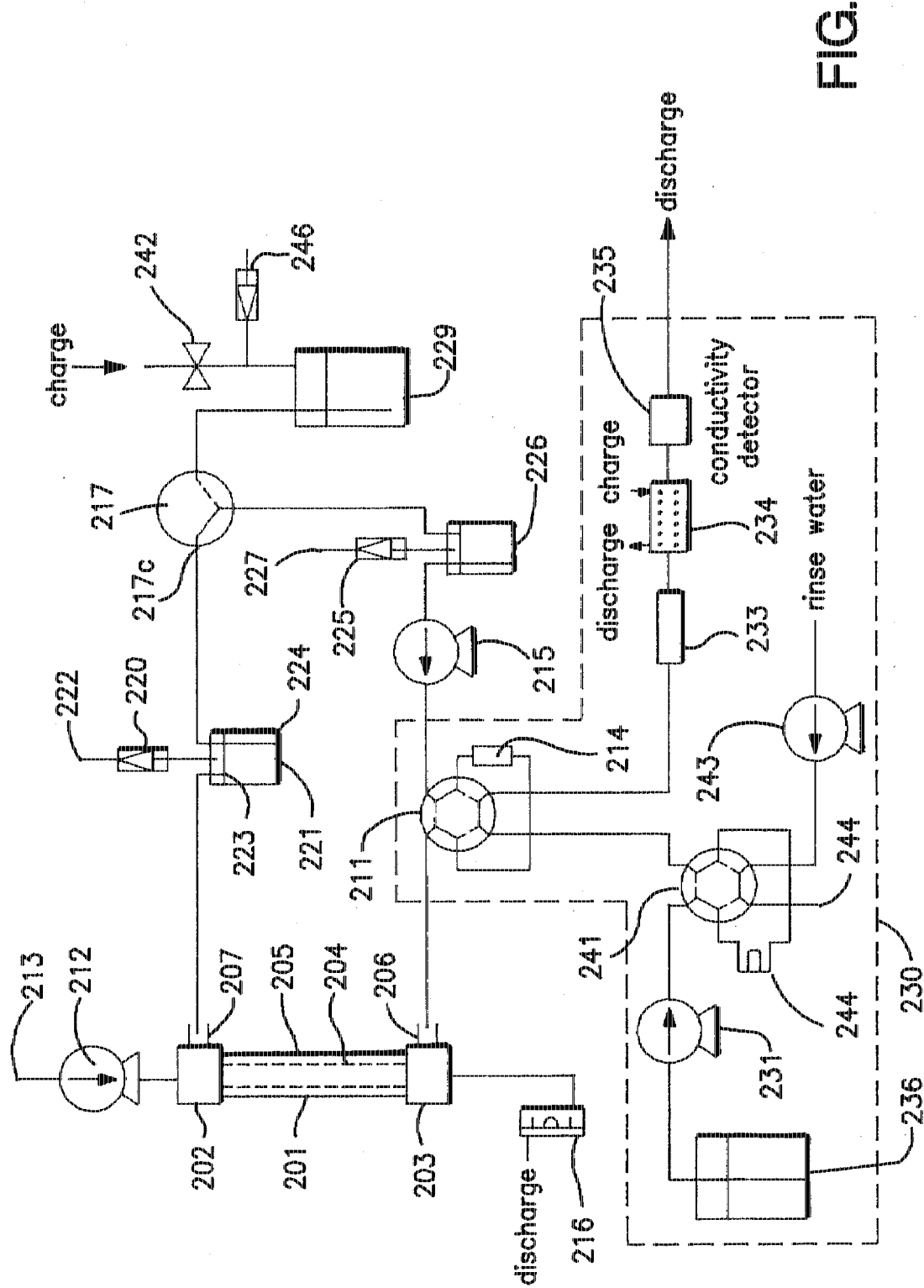
FIG. 7 is a diagram illustrative of a novel gas component analyzing system having a diffusion scrubber and a chromatograph in a fourth embodiment according to the present invention.

As illustrated in FIG. 7, the novel gas component analyzing system comprises a gas collection system and an ion chromatograph 230 for analyzing an ammonia component in an atmosphere. A significant structural difference of the system in the fourth embodiment from that of the first embodiment is in further providing a rinse water injection valve and a rinse water pump and providing no guard column. In this embodiment, the rinse water injection valve is inserted into between an eluate pump and a sample injection valve.

The gas collection system includes a diffusion scrubber 201. The diffusion scrubber 201 further comprises an inner tube 204 and an outer tube 205. The inner tube 204 comprises a micro-porous fluororesin membrane tube (Porflon tube TB-32) having a length of 50 cm and being provided at its opposite ends with fluororesin tubes. The micro-porous fluororesin membrane tube allows gases to penetrate through the micro-porous, but prevent any liquid from penetrating through the same. The outer tube 205 comprises a fluororesin tube having a length of 70 cm and inner and outer diameters of 4 mm and 6 mm respectively. The inner and outer tubes 204 and 205 are fixed to one another through joint members 202 and 203 provided at longitudinally opposite ends of the both tubes. Structures of the joint members 202 and 203 are illustrated in FIG. 5.

The diffusion scrubber 201 is coupled through its gas inlet port to a sampling gas pump 212 which is further coupled to a gas inlet port 213 so that sampling gases are fed through the sampling gas pump 212 into the inside of the inner tube 204. The gases are fed to a flow meter 216 and then discharged.

The diffusion scrubber 201 is coupled through its absorption liquid inlet port 206 to a sample injection valve 211. The sample injection valve 211 has six way passages and six connective ports. The six connective ports are named as first to sixth connective ports in a clockwise direction for convenience of the following description. The absorption liquid inlet port 206 of the diffusion scrubber 201 is coupled to a first connective port of the sample injection valve 211. The sample injection valve 211 is provided with a concentration column (Ion Pac CG12) 214 through its third and sixth connective ports. In the concentration column 214, the gas components captured in the absorption liquid is concentrated.

The sample injection valve 211 is also coupled to an absorption liquid pump 215 which is further coupled to a defoamer 226 for removing any foam from the absorption liquid. The defoamer 226 is provided with a discharge port 227 from which a part of the absorption Liquid in the defoamer 226 is discharged together with air or foam in the liquid. The discharge port 227 is provided with a check valve 225. The defoamer 226 is coupled through its outlet pipe to the absorption liquid pump 215 and also coupled through its inlet pipe to a flow passage switch valve 217. The flow passage switch valve 217 has three way passages and three connective ports. The three connective ports are herein named as first to third ports. The flow passage switch valve 217 is coupled through the first port to the defoamer 226. The flow passage switch valve 217 is also coupled through the second port to another defoamer 221. The defoamer 221 has a discharge port 222 with a check valve 220 so that a part of the absorption liquid in the defoamer 221 is discharged together with air or foam in the liquid from the discharge port 222. The defoamer 221 also has an inlet pipe 223 coupled to the inlet port 207 of the diffusion scrubber 201 and an outlet pipe 224 connected to the second port of the flow passage switching valve 217. The flow passage switching valve 217 is coupled through its third port to an absorption liquid reserver 229 in which an absorption liquid is reserved. In this embodiment, the absorption liquid is a super pure water.

The flow passage switch valve 217 comes to take a first state in which the flow passage is formed between the first and second ports so that the first and second ports are connected one another. In this first state, there is formed a circulation absorption liquid flow passage. The flow passage switch valve 217 comes to take a second state in which the flow passage is formed between the first and third ports so that the first and third ports are connected one another. In this second state, there is formed a non-circulation absorption liquid flow passage.

The ion chromatograph (DX100) 230 includes a series of a separation column (Ion Pac CS12). 233, a suppresser (CSRS-I) 234 coupled to the separation column 233 and the electrical conductivity detector 235 coupled to the suppresser 234. The separation column 233 is connected to the fourth port of the sample injection valve 211.

The rinse water injection valve 241 is provided between the sample injection valve 211 and an eluate pump 231 which is further coupled to an eluate reservoir 236 in which 20 mM of methylsulfonic acid as the elute is reserved. The rinse water injection valve 241 has six way flow passages and six connective ports which are named as first to sixth ports in a clockwise direction. The first port of the rinse water injection valve is coupled to the eluate pump 231. The second port of the rinse water injection valve 241 is coupled to the fifth port of the sample injection vale 211. The rinse water injection valve 241 is further coupled through its third and sixth ports to a rinse water measuring slender tube 244. The fourth port of the rinse water injection valve 241 is coupled to a rinse water pump 243 for feeding the rinse water into the rinse water injection valve 241. The fifth port of the rinse water injection valve 241 is coupled to a discharge port 242 from which the rinse water is discharged.

Moreover, there is provided a control unit 44 including a computer 44a and an interface 44b connected to the computer 44a. Detection data detected by the detector in the ion chromatograph are fetched and inputted through the interface 44b into the computer 44a for subsequent generation of control signals to be transmitted to individual valves and pumps for controlling motions thereof as illustrated in FIG. 4.

The flow passage for the absorption liquid switches between the circulation flow passage and the non-circulation flow passage. The flow passage for the elute switches between the analyzing flow passage and non-analyzing flow passage.

The flow passage for the rinse water switches between the rinse water feeding passage and the rinse water non-feeding passage.

The following descriptions will focus on the operations of the above described gas component analyzing system. The flow passage switch valve 217 is switched to have the absorption liquid flow passage come into the non-circulation passage. Further, the sample injection valve 211 is switched to have the elute flow passage come into the non-analyzing flow passage and the rinse water injection valve 241 is switched to have the rinse water flow passage come into the rinse water non-feeding passage so that the rinse water is fed by the rinse water pump into the rinse water measuring slender tube 244 and pooled therein.

A valve 247 is set open for feeding nitrogen gas into the absorption liquid reserver 229. The absorption liquid pump 215 is placed into operation as well as the rinse water pump 231 is put in operation. Further, the ion chromatograph 230 is put in operation. The absorption liquid, for example, the super pure water is fed from the absorption liquid reserver 229 through the defoamer 226 into the absorption liquid pump 215. In the defoamer 226, a part of the absorption liquid is discharged from the discharge port 227 together with the air in the defoamer 226 and the remaining absorption liquid is fed to the absorption liquid pump 215.

After discharge of the air from the defoamer 226, the valve 247 closes, while there are still kept the flow passage switch valve 217, the sample injection valve 211, the rinse water pump 243 and the absorption liquid pump 215. An atmosphere is suctioned by the sampling gas pump 212 to have the atmosphere pass through the inside of the inner tube 204 of the diffusion scrubber 201. An amount of the suctioned atmosphere is controlled by the flow meter 216 for nine and a half minutes. The absorption liquid is introduced into the inlet port 206 of the diffusion scrubber 201 and then charged between the inner and outer tubes 204 and 205, resulting in an overflow of the absorption liquid and subsequent discharge thereof from the outlet port 207. The overflowed and discharged absorption liquid is fed to the defoamer 221. Since the second port of the flow passage switch valve is closed, the absorption liquid is discharged from the discharge port 222 together with air in the defoamer 221. As a result, the defoamer 221 is filled with the absorption liquid. The absorption liquid between the outlet port 207 of the diffusion scrubber 201 and the defoamer 221 comes into an equilibrium state in ammonia to the sampling atmosphere passing through the diffusion scrubber 201. Meanwhile, the rinse water measuring slender tube 244 is filled with the rinse water. The above previous step is maintained for nine and a half minutes.

After the above previous process is completed, the rinsing process is commenced. The rinse water injection valve 241 is switched to have the rinse water flow passage come into the rinse water feeding flow passage so that the rinse water is fed together with the eluate through the sample injection valve 211 to the concentration column 214. The rinse water passes through the fifth port and the sixth port and then injected into the concentration column 214 thereby rinsing and removing the eluate from the concentration column 214. This rinsing process is continued for a half minute until no rinse water remains in the rinse water measuring slender tube 244. A capacity of the rinse water measuring slender tube 244 is defined by the product of the flow rate associated with the elute pump 231.

After the above rinsing process is completed, the sampling process is commenced. The flow passage switch valve 217 and the sample injection valve 211 are switched to have the absorption liquid flow passage to come into the circulation flow passage or the sampling flow passage so that the absorption liquid passes through the concentration column 214 thereby conducting a concentration of the analyzing gas components. The rinse water injection valve 241 is switched to have the rinse water flow passage come into the rinse water feeding flow passage so that the rinse water in pooled in the rinse water measuring slender tube 244 is fed together with the eluate through the sample injection valve 211 into the separation column without however passing through the concentration column 214. This sampling process is continued for ten minutes. Since the absorption liquid flow passage have come into the circulation flow passage, the absorption liquid in the defoamer 221 is fed through the flow passage switch valve 217 to the defoamer 226. In the diffusion scrubber 201, the absorption liquid shows an absorption of gas components including at least ammonia. This absorption liquid is fed through the circulation flow passage into the concentration column 214 where ammonia component is absorbed into an absorbent of the concentration column and then concentrated. Then, the absorption liquid is circulated to the diffusion scrubber 201 for further absorption of the ammonia gas component. Since the absorption liquid is kept circulated during the sampling process, a no-load running test value is kept constant. This means that a long time sampling results in an improvement in S/B ratio thereby a detectable minimum vale is lowered.

After the above sampling process is completed, the analyzing process is commenced. The flow passage switch valve 217 is switched to have the absorption liquid flow passage come into the non-circulation flow passage. The rinse water injection valve 241 is switched to have the rinse water flow passage come into the non-feeding flow passage thereby the rinse water is injected into the rinse water measuring slender tube 244 and pooled therein. The sample injection valve 211 is switched to have the eluate flow passage come into the analyzing flow passage. As a result, the eluate reserved in the eluate reservoir 236 is fed through the eluate pump 231 to the concentration column 214 where the eluate may cause an elution of the concentrated ammonia, which has been concentrated in the concentration column 214 in the sampling process. The eluted ammonia is then fed together with the eluate to the separation column 233 where ammonia component is separated from other anion components. The ammonia component is then fed to the suppresser 234 where an electrical conductivity of background is reduced. The ammonia component is then fed to the electrical conductivity detector 235 for measurement of the electrical conductivity. A variation in conductivity versus time is inputted as data through the interface 44b into the computer 44a in the control unit 44 illustrated in FIG. 4. From the inputted data, the computer 44a sequentially conduct the required preparation of the chromatograph, a detection of peak with respect to ammonia, a computation of peak area, a computation of ammonia concentration in the sample atmosphere and output of resultant data via a screen or a printer.

Meanwhile, during the above analyzing process, on the non-circulation flow passage for the absorption liquid, the previous process is carried out as the next process.

The above analyzing process is continued for nine and a half minutes, after which the flow passage switch valve 217, the rinse water injection valve 241 and the sample injection valve 211 are switched to enter into the rinsing process. Subsequently, in accordance with the number for successive measurements predetermined by the computer 44a, the above rinsing, sampling and analyzing processes are in turn repeated for successive measurements of ammonia in the atmosphere every twenty minutes.

As modifications, the above system may come available to detect acid components in the atmosphere by replacing the individual columns in the ion chromatograph 230. The above system may also become available to detect various volatile components by use of the flow injection analyzing or the liquid chromatograph, or various analyzer available to be coupled thereof. It is also available to add a further gas collection system so that the gas analyzer system comprises two gas collection systems and a single ion chromatograph like the third embodiment.

A fifth embodiment according to the present invention will be described in detail with reference to FIG. 8 in which there is provided a novel gas component analyzing system having a diffusion scrubber and an ion chromatograph.

Figure 8:
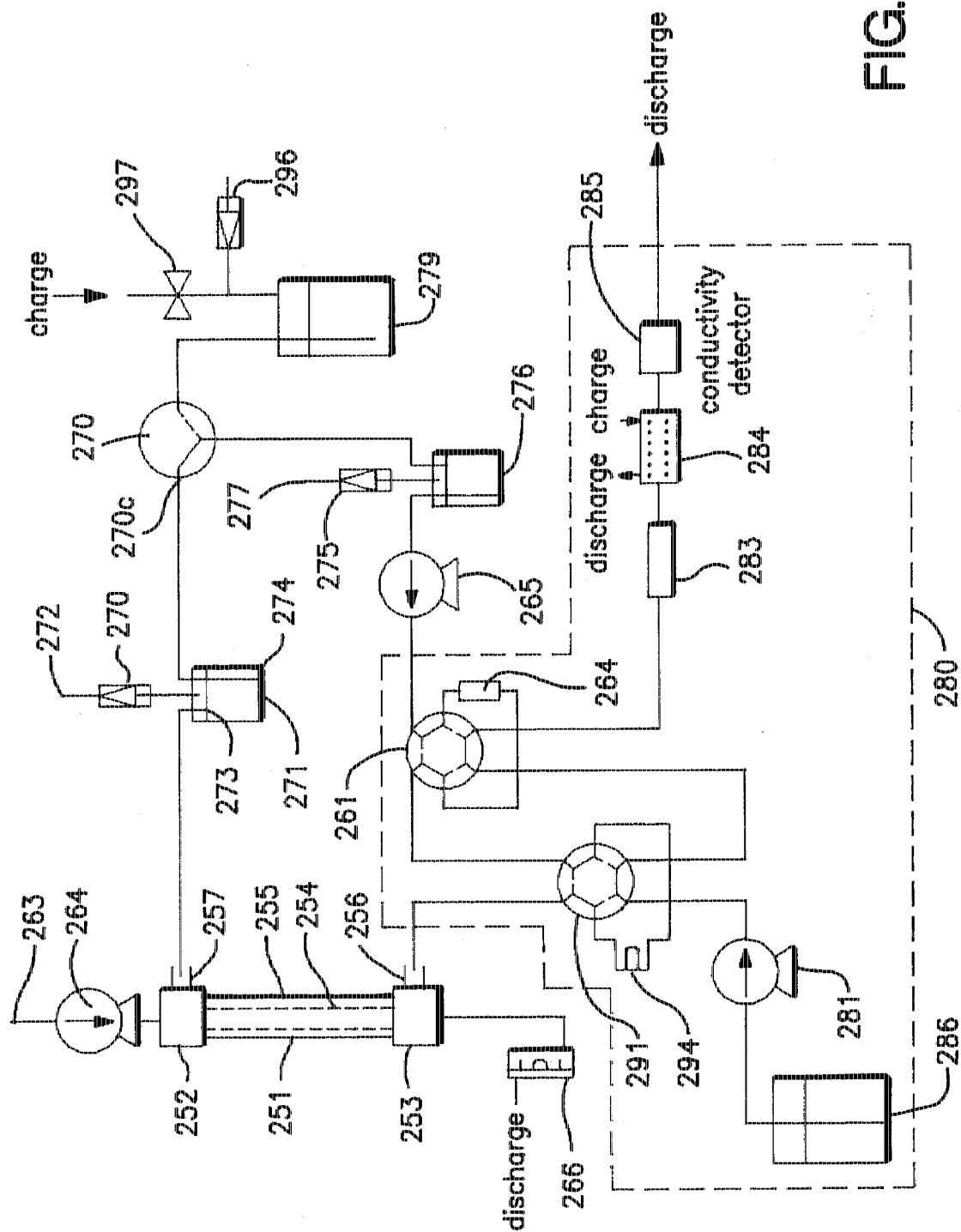
FIG. 8 is a diagram illustrative of a novel gas component analyzing system having a diffusion scrubber and a chromatograph in a fifth embodiment according to the present invention.

As illustrated in FIG. 8, the novel gas component analyzing system comprises a gas collection system and an ion chromatograph 280 for analyzing an ammonia component in an atmosphere. A significant structural difference of the system in the fourth embodiment from that of the fourth embodiment is both in providing further connections of the rinse water injection valve to both the sample injection valve and the absorption liquid inlet port of he diffusion scrubber and in providing no rinse water pump. The eluate may further serve as a rinse water.

The gas collection system includes a diffusion scrubber 251. The diffusion scrubber 251 further comprises an inner tube 254 and an outer tube 255. The inner tube 254 comprises a micro-porous fluororesin membrane tube (Porflon tube TB-32) having a length of 50 cm and being provided at its opposite ends with fluororesin tubes. The micro-porous fluororesin membrane tube allows gases to penetrate through the micro-porous, but prevent any liquid from penetrating through the same. The outer tube 255 comprises a fluororesin tube having a length of 70 cm and inner and outer diameters of 4 mm and 6 mm respectively. The inner and outer tubes 254 and 255 are fixed to one another through joint members 252 and 253 provided at longitudinally opposite ends of the both tubes. Structures of the joint members 252 and 253 are illustrated in FIG. 5.

The diffusion scrubber 251 is coupled through its gas inlet port to a sampling gas pump 262 which is further coupled to a gas inlet port 263 so that sampling gases are fed through the sampling gas pump 262 into the inside of the inner tube 254. The gases are fed to a flow meter 266 and then discharged.

The diffusion scrubber 251 is coupled through its absorption liquid inlet port 256 to a rinse water injection valve 291 which is further coupled to a sample injection valve 261. The rinse water injection valve 291 has six way passages and six connective ports. The six connective ports are named as first to sixth connective ports in a clockwise direction for convenience of the following description. The sample injection valve 261 also has six way passages and six connective ports. The six connective ports are named as first to sixth connective ports in a clockwise direction for convenience of the following description. The absorption liquid inlet port 256 of the diffusion scrubber 251 is coupled to a first connective port of the rinse water injection valve 291. The second port of the rinse water injection valve 291 is coupled to the first port of the sample injection valve 261. The fourth port of the rinse water injection valve 291 is coupled to the fifth port of the sample injection vale 261. The fifth port of the rinse water injection valve 291 is coupled through an eluate pump 281 to an eluate reservoir 286 in which 20 mM of methylsulfonic acid as the eluate is reserved. The rinse water injection valve 291 is further coupled through its third and sixth ports to a rinse water measuring slender tube 294.

The sample injection valve 261 is provided with a concentration column (Ion Pac CG12) 264 through its third and sixth connective ports. In the concentration column 264, the gas components captured in the absorption liquid is concentrated.

The sample injection valve 261 is also coupled through its second port to an absorption liquid pump 265 which is further coupled to a defoamer 276 for removing any foam from the absorption liquid. The defoamer 276 is provided with a discharge port 277 from which a part of the absorption liquid in the defoamer 276 is discharged together with air or foam in the liquid. The discharge port 277 is provided with a check valve 275. The defoamer 276 is coupled through its outlet pipe to the absorption liquid pump 265 and also coupled through its inlet pipe to a flow passage switch valve 267. The flow passage switch valve 267 has three way passages and three connective ports. The three connective ports are herein named as first to third ports. The flow passage switch valve 267 is coupled through the first port to the defoamer 276. The flow passage switch valve 267 is also coupled through the second port to another defoamer 271. The defoamer 271 has a discharge port 272 with a check valve 270 so that a part of the absorption liquid in the defoamer 271 is discharged together with airs or foam in the liquid from the discharge port 272. The defoamer 271 also has an inlet pipe 273 coupled to the inlet port 257 of the diffusion scrubber 251 and an outlet pipe 274 connected to the second port of the flow passage switching valve 267. The flow passage switching valve 267 is coupled through its third port to an absorption liquid reserver 279 in which an absorption liquid is reserved. In this embodiment, the absorption liquid is a super pure water.

The flow passage switch valve 267 comes to take a first state in which the flow passage is formed between the first and second ports so that the first and second ports are connected to one another. In this first state, there is formed a circulation absorption liquid flow passage. The flow passage switch valve 267 comes to take a second state in which the flow passage is formed between the first and third ports so that the first and third ports are connected one another. In this second state, there is formed a non-circulation absorption liquid flow passage.

The ion chromatograph (DX100) 280 includes a series of a separation column (Ion Pac CS12) 283, a suppresser (CSRS-I), 284 coupled to the separation column 283 and the electrical conductivity detector 235 coupled to the suppresser 234. The separation column 233 is connected to the fourth port of the sample injection valve 261.

Moreover, there is provided a control-unit 44 including a computer 44a and an interface 44b connected to the computer 4a. Detection data detected by the detector in the ion chromatograph are fetched and inputted through the interface 4b into the computer 44a for subsequent generation of control signals to be transmitted to individual valves and pumps for controlling motions thereof as illustrated in FIG. 4.

The flow passage for the absorption liquid switches between the circulation flow passage and the non-circulation flow passage. The flow passage for the elute switches between the analyzing flow passage and non-analyzing flow passage.

The following descriptions will focus on the operations of the above described gas component analyzing system. The flow passage switch valve 267 is switched to have the absorption liquid flow passage come into the non-circulation passage. Further, the sample injection valve 261 and the rinse water injection valve 291 are switched to have the rinse water eluate flow passage come into the non-feeding passage so that the eluate and the rinse water are fed by the rinse water pump into the rinse water measuring slender tube 294 and pooled therein.

A valve 297 is set open for feeding nitrogen gas into the absorption liquid reserver 279. The absorption liquid pump 265 is placed into operation as well as the rinse water pump 281 is put in operation. Further, the ion chromatograph 280 is put in operation. The absorption liquid, for example, the super pure water is fed from the absorption liquid reserver 279 through the defoamer 276 into the absorption liquid pump 265. In the defoamer 276, a part of the absorption liquid is discharged from the discharge port 277 together with the air in the defoamer 276 and the remaining absorption liquid is fed to the absorption liquid pump 265.

After discharge of the air from the defoamer 276, the valve 297 closes, while there are still kept the flow passage switch valve 267, the sample injection valve 261, the rinse water pump 293 and the absorption liquid pump 265. An atmosphere is suctioned by the sampling gas pump 262 to have the atmosphere pass through the inside of the inner tube 254 of the diffusion scrubber 251. An amount of the suctioned atmosphere is controlled by the flow meter 266 for nine and a half minutes. The absorption liquid is introduced into the inlet port 256 of the diffusion scrubber 251 and then charged between the inner and outer tubes 254 and 255, resulting in an overflow of the absorption liquid and subsequent discharge thereof from the outlet port 257. The overflowed and discharged absorption liquid is fed to the defoamer 271. Since the second port of the flow passage switch valve is closed, the absorption liquid is discharged from the discharge port 272 together with air in the defoamer 271. As a result, the defoamer 271 is filled with the absorption liquid. The absorption liquid between the outlet port 257 of the diffusion scrubber 251 and the defoamer 271 comes into an equilibrium state in ammonia to the sampling atmosphere passing through the diffusion scrubber 251. Meanwhile, the rinse water measuring-slender tube 294 is filled with the rinse water and the eluate. The above previous step is maintained for nine and a half minutes.

After the above previous progress is completed, the rinsing process is commenced. The rinse water injection valve 291 is switched to have the rinse water elute flow passage come into the feeding flow passage so that the rinse water and the eluate are fed through the sample injection valve 261 to the concentration column 264. The rinse water passes through the fifth port and the sixth port and then injected into the concentration column 264. This rinsing process is continued for a half minute until no rinse water remains in the rinse water measuring slender tube 294. A capacity of the rinse water measuring slender tube 294 is defined by the product of the flow rate associated with the eluate pump 281.

After the above rinsing process is completed, the sampling process is commenced. The flow passage switch valve 267 and the sample injection valve 261 are switched to have the absorption liquid flow passage to come into the circulation flow passage or the sampling flow passage so that the absorption liquid passes through the concentration column 264 thereby conducting a concentration of the analyzing gas components. The rinse water injection valve 291 is switched to have the rinse water flow passage come into the rinse water feeding flow passage so that the rinse water or the eluate pooled in the rinse water measuring slender tube 294 is fed through the sample injection valve 261 into the separation column without however passing through the concentration column 264. This sampling process is continued for ten minutes. Since the absorption liquid flow passage has come into the circulation flow passage the absorption liquid in the defoamer 271 is fed through the flow passage switch valve 267 to the defoamer 276. In the diffusion scrubber 251, the absorption liquid shows an absorption of gas components including at least ammonia. This absorption liquid is fed through the circulation flow passage into the concentration column 264 where ammonia component is absorbed into an absorbent of the concentration column and then concentrated. Then, the absorption liquid is circulated to the diffusion scrubber 251 for further absorption of the ammonia gas component. Since the absorption liquid is kept circulated during the sampling process, a no-load running test value is kept constant. This means that a long time sampling results in an improvement in S/B ratio thereby a detectable minimum vale is lowered.

After the above sampling process is completed, the analyzing process is commenced. The flow passage switch valve 267 is switched to have the absorption liquid flow passage come into the non-circulation flow passage. The rinse water injection valve 291 and the sample injection valve 261 are switched to have the eluate flow passage come into the analyzing flow passage. As a result, the eluate or the rinse water reserved in the eluate reservoir 286 is fed through the eluate pump 281 to the concentration column 264 where the eluate may cause an elution of the concentrated ammonia, which has been concentrated in the concentration column 264 in the sampling process. The eluted ammonia is then fed together with the eluate to the separation column 283 where ammonia component is separated from other anion components. The ammonia component is then fed to the suppresser 284 where an electrical conductivity of background is reduced. The ammonia component is then fed to the electrical conductivity detector 285 for measurement of the electrical conductivity. A variation in conductivity versus time is inputted as data through the interface 44b into the computer 44a in the control unit 44 illustrated in FIG. 4. From the inputted data, the computer 44a sequentially conduct the required preparation of the chromatograph, a detection of peak with respect to ammonia, a computation of peak area, a computation of ammonia concentration in the sample atmosphere and output of resultant data via a screen or a printer.

Meanwhile, during the above analyzing process, on the non-circulation flow passage for the absorption liquid, the previous process is carried out as the next process.

The above analyzing process is continued for nine and a half minutes, after which the flow passage switch valve 267, the rinse water injection valve 291 and the sample injection valve 261 are switched to enter into the rinsing process. Subsequently, in accordance with the number for successive measurements predetermined by the computer 44a, the above rinsing, sampling and analyzing processes are in turn repeated for successive measurements of ammonia in the atmosphere every twenty minutes.

As modifications, the above system may become available to detect acid components in the atmosphere by replacing the individual columns in the ion chromatograph 280. The above system may also become available to detect various volatile components by use of the flow injection analyzing or the liquid chromatograph, or various analyzer available to be coupled thereof. It is also available to add a further gas collection system so that the gas analyzer system comprises two gas collection systems and a single ion chromatograph like the third embodiment.

A sixth embodiment according to the present invention will be described in detail with reference to FIG. 9 in which there is provided a novel gas component analyzing system having a diffusion scrubber and an ion chromatograph.

Figure 9:
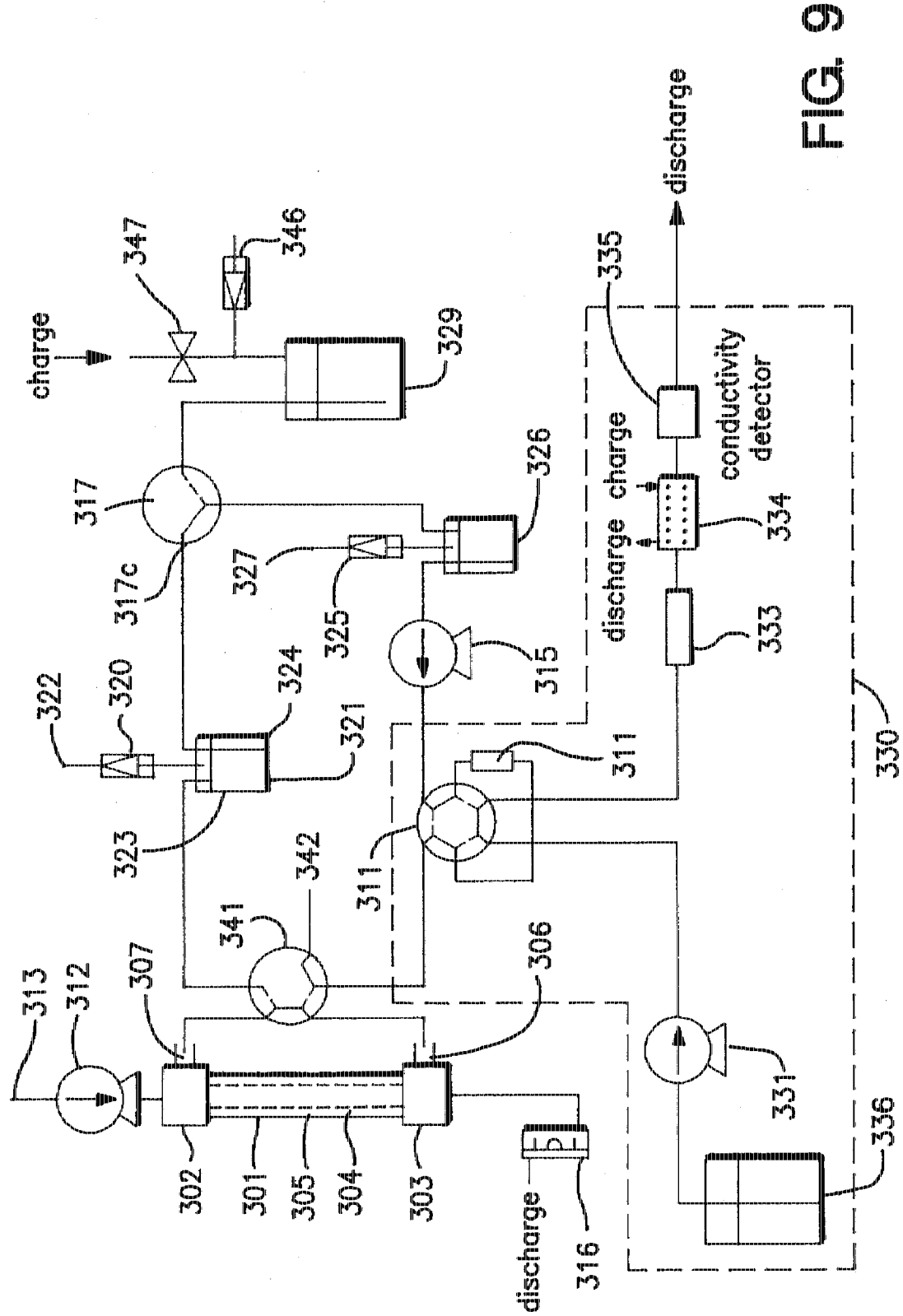
FIG. 9 is a diagram illustrative of a novel gas component analyzing system having a diffusion scrubber and a chromatograph in a sixth embodiment according to the present invention.

As illustrated in FIG. 9, the novel gas component analyzing system comprises a gas collection system and an ion chromatograph 330 for analyzing an ammonia component in an atmosphere. A significant structural difference of the system in the sixth embodiment from that of the fifth embodiment is in a position at which the rinse water injection valve is provided so that the absorption liquid may further serve as a rinse water.

As illustrated in FIG. 9, the novel gas component analyzing system comprises a gas collection system and an ion chromatograph 330 for analyzing an ammonia component in an atmosphere. A significant structural difference of the system in the fourth embodiment from that of the first embodiment is in further providing a rinse water injection valve and a rinse water pump and providing no guard column. In this embodiment, the rinse water injection valve is inserted into between an eluate pump and a sample injection valve.

The gas collection system includes a diffusion scrubber 301. The diffusion scrubber 301 further comprises an inner tube 304 and an outer tube 305. The inner tube 304 comprises a micro-porous fluororesin membrane tube (Porflon tube TB-32) having a length of 50 cm and being provided at its opposite ends with fluororesin tubes. The micro-porous fluororesin membrane tube allows gases to penetrate through the micro-porous, but prevent any liquid from penetrating through the same. The outer tube 305 comprises a fluororesin tube having a length of 70 cm and inner and outer diameters of 4 mm and 6 mm respectively. The inner and outer tubes 304 and 305 are fixed to one another through joint members 302 and 303 provided at longitudinally opposite ends of the both tubes. Structures of the joint members 302 and 303 are illustrated in FIG. 5.

The diffusion scrubber 301 is coupled through its gas inlet port to a sampling gas pump 312 which is further coupled to a as inlet port 313 so that sampling gases are fed through the sampling gas pump 312 into the inside of the inner tube 304. The gases are fed to a flow meter 316 and then discharged.

The diffusion scrubber 301 is coupled through its absorption liquid inlet port 306 through a rinse water injection valve 341 to a sample injection valve 311. The rinse water injection valve 341 has five way flow passages and five connective ports which are named as first to fifth ports in a clockwise direction. The sample injection valve 311 has six way passages and six connective ports. The six connective ports are named as first to sixth connective ports in a clockwise direction. The first port of the rinse water injection valve 341 is coupled to a discharge port 342 from which the rinse water is discharged. The second port of the rinse water injection valve 341 is coupled to the first port of the sample injection vale 311. The third connective port of the rinse water injection valve 341 is coupled to the absorption liquid inlet port 306 of the diffusion scrubber 301. The fourth connective port of the rinse water injection valve 341 is coupled to the absorption liquid outlet port 307 of the diffusion scrubber 301. The fifth connective port of the rinse water injection valve 341 is coupled to a defoamer 321.

The fifth connective port of the sample injection valve 311 is coupled to an eluate pump 331 which is further coupled to an eluate reservoir 336 in which 20 mM of methylsulonic acid as the eluate is reserved. The sample injection valve 311 is provided with a concentration column (Ion Pac CG12) 314 through its third and sixth connective ports. In the concentration column 314, the gas components captured in the absorption liquid are concentrated.

The sample injection valve 311. is also coupled to an absorption liquid pump 315 which is further coupled to a defoamer 326 for removing any foam from the absorption liquid. The defoamer 326 is provided with a discharge port 327 from which a part of the absorption liquid in the defoamer 326 is discharged together with air or foam in the liquid. The discharge port 327 is provided with a check valve 325. The defoamer 326 is coupled through its outlet pipe to the absorption liquid pump 315 and also coupled through its inlet pipe to a flow passage switch valve 317. The flow passage switch valve 317 has three way passages and three connective ports. The three connective ports are herein named as first to third ports. The flow passage switch valve 317 is coupled through the first port to the defoamer 326. The flow passage switch valve 317 is also coupled through the second port to the defoamer 321. The defoamer 321 has a discharge port 322 with a check valve 320 so that a part of the absorption liquid in the defoamer 321 is discharged together with air or foam in the liquid from the discharge port 322. The defoamer 321 also has an inlet pipe 323 coupled to the fifth connective port of the rinse water injection valve 341 and an outlet pipe 324 connected to the second port of the flow passage switching valve 317. The flow passage switching valve 317 is coupled through its third port to an absorption liquid reservoir 329 in which an absorption liquid is reserved. In this embodiment, the absorption liquid is a super pure water and may serve as a rinse water.

The flow passage switch valve 317 comes to take a first state in which the flow passage is formed between the first and second ports so that the first and second ports are connected to one another. In this first state, there is formed a circulation absorption liquid flow passage. The flow passage switch valve 317 comes to take a second state in which the flow passage is formed between the first and third ports so that the first and third ports are connected to one another. In this second state, there is formed a non-circulation absorption liquid flow passage.

The ion chromatograph (DX100) 330 includes a series of a separation column (Ion Pac CS12) 333, a suppresser (CSRS-I) 334 coupled to the separation column 333 and the electrical conductivity detector 335 coupled to the suppresser 334. The separation column 333 is connected to the fourth port of the sample injection valve 311.

Moreover, there is provided a control unit 44 including a computer 44a and an interface 44b connected to the computer 44a. Detection data detected by the detector in the ion chromatograph are fetched and inputted through the interface 44b into the computer 44a for subsequent generation of control signals to be transmitted to individual valves and pumps for controlling motions thereof as illustrated in FIG. 4.

The flow passage for the absorption liquid switches between the circulation flow passage and the non-circulation flow passage. The flow passage for the eluate switches between the analyzing flow passage and non-analyzing flow passage.

The following descriptions will focus on the operations of the above described gas component analyzing system. The flow passage switch valve 317 is switched to have the absorption liquid flow passage come into the non-circulation passage. Further, the sample injection valve 311 is switched to have the eluate flow passage come into the non-analyzing flow passage and the rinse water injection valve 341 is switched to feed the absorption liquid or the rinse water to the diffusion scrubber 301.

A valve 347 is set open for feeding nitrogen gas into the absorption liquid reserver 329. The absorption liquid pump 315 is placed into operation. Further, the ion chromatograph 330 is put in operation. The absorption liquid, for example, the super pure water is fed from the absorption liquid reservoir 329 through the defoamer 326 into the absorption liquid pump 315. In the defoamer 326, a part of the absorption liquid is discharged from the discharge port 327 together with the air in the defoamer 326 and the remaining absorption liquid is fed to the absorption liquid pump 315.

After discharge of the air from the defoamer 326, the valve 347 closes, while there are still kept the flow passage switch valve 317, the sample injection valve 311 and the absorption liquid pump 315. An atmosphere is suctioned by the sampling gas pump 312 to have the atmosphere pass through the inside of the inner tube 304 of the diffusion scrubber 301. An amount of the suctioned atmosphere is controlled by the flow meter 316 for nine and a half minutes. The absorption liquid is introduced into the inlet port 306 of the diffusion scrubber 301 and then charged between the inner and outer tubes 304 and 305, resulting in an overflow of the absorption liquid and subsequent discharge thereof from the outlet port 307. The overflowed and discharged absorption liquid is fed to the defoamer 321. Since the second port of the flow passage switch valve is closed, the absorption liquid is discharged from the discharge port 322 together with any air in the defoamer 321. As a result, the defoamer 321 is filled with the absorption liquid. The absorption liquid between the outlet port 307 of the diffusion scrubber 301 and the defoamer 321 comes into an equilibrium state in ammonia to the sampling atmosphere passing through the diffusion scrubber 301. The above previous step is maintained for nine and a half minutes.

After the above previous process is completed, the rinsing process is commenced. The rinse water injection valve 341 is switched to separate the diffusion scrubber from the sample injection valve 311 and from the defoamer 321 as well as the sample injection valve 311 is switched to connect the concentration column 314 to the absorption liquid pump 315 so that the absorption liquid serving as the rinse water is fed to the concentration column 314. The absorption liquid injected into the concentration column 314 may rinse and remove the eluate from the concentration column 314. This rinsing process is continued for a half minute during which the absorption liquid remains in the diffusion scrubber 301 and the gas sampling pump 312 remains in the operation state. The diffusion scrubber 301 is kept in operation whereby the sampling gas components are absorbed into the absorption liquid.

After the above rinsing process is completed, the sampling process is commenced. The flow passage switch valve 317 is switched to connect the defoamers 321 and 324 to one another. The rinse water injection valve 341 is switched to connect the sample injection valve 311 to the absorption liquid inlet port 306 of the diffusion scrubber 301 and to connect the absorption liquid outlet port 307 of the diffusion scrubber 301 to the defoamer 321. As a result, the absorption liquid having absorbed the sampling gas components is fed to the concentration column 314 where the gas components are absorbed onto the absorbent in the concentration column 314 and then concentrated therein. This sampling process is continued for nine and a half minutes. Since the absorption liquid flow passage has come into the circulation flow passage, the absorption liquid in the defoamer 321 is fed through the flow passage switch valve 317 to the defoamer 326. In the diffusion scrubber 301, the absorption liquid shows an absorption of gas components including at least ammonia. This absorption liquid is fed through the circulation flow passage into the concentration column 314 where ammonia component is absorbed into an absorbent of the concentration column and then concentrated. Then, the absorption liquid is circulated to the diffusion scrubber 301 for further absorption of the ammonia gas component. Since the absorption liquid is kept circulated during the sampling process, a no-load running test value is kept constant. This means that a long time sampling results in an improvement in S/B ratio thereby a detectable minimum valve is lowered.

After the above sampling process is completed, the analyzing process is commenced. The flow passage switch valve 317 is switched to have the absorption liquid flow passage come into the non-circulation flow passage. The sample injection valve 311 is switched to connect the concentration column 314 to the eluate flow passage and separate the concentration column 314 from the absorption liquid flow passage. As a result, the eluate reserved in the eluate reservoir 336 is fed through the eluate pump 331 to the concentration column 314 where the eluate may cause an elution of the concentrated ammonia, which has been concentrated in the concentration column 314 in the sampling process. The eluted ammonia is then fed together with the eluate to the separation column 333 where ammonia component is separated from other anion components. The ammonia component is then fed to the suppresser 334 where an electrical conductivity of background is reduced. The ammonia component is then fed to the electrical conductivity detector 335 for measurement of the electrical conductivity. A variation in conductivity versus time is inputted as data through the interface 44b into the computer =44a in the control unit 44 illustrated in FIG. 4. From the inputted data, the computer 44a sequentially conduct the required preparation of the chromatograph, a detection of peak with respect to ammonia, a computation of peak area, a computation of ammonia concentration in the sample atmosphere and output of resultant data via a screen or a printer.

Meanwhile, during the above analyzing process, on the non-circulation flow passage for the absorption liquid, the previous process is carried out as the next process.

The above analyzing process is continued for nine and a half minutes, after which the flow passage switch valve 317, the rinse water injection valve 341 and the sample injection valve 311 are switched to enter into the rinsing process. Subsequently, in accordance with the number of successive measurements predetermined by the computer 44a, the above rinsing, sampling and analyzing processes are in turn repeated for successive measurements of ammonia in the atmosphere every nineteen and a half minutes.

As modifications, the above system may become available to detect acid components in the atmosphere by replacing the individual columns in the ion chromatograph 330. The above system may also come available to detect various volatile components by use of the flow injection analyzing or the liquid chromatograph, or various analyzer available to be coupled thereof. It is also available to add a further gas collection system so that the gas analyzer system comprises two gas collection systems and a single ion chromatograph like the third embodiment.

Whereas further modifications of the present invention will no doubt be apparent to a person having ordinary skill in the art, to which the invention pertains, it is to be understood that embodiments show and described by way of illustrations are by no means intended to be considered in a limiting sense. Accordingly, it is intended to cover by claims any modifications of the present invention, which fall within the spirit and scope of the invention.

What is claimed is:

1. An apparatus for collecting gas components comprising:

a diffusion scrubber comprising an inner tube and an outer tube, said inner tube comprising a gas penetrating membrane through which sampling gases only may penetrate, wherein sampling gases flow through inside of said inner tube and an absorption liquid flows through between said inner and other tubes so that said absorption liquid absorbs said sampling gases penetrated through said membrane from the inside of the inner tube;

an absorption liquid feeding pump upstream from said diffusion scrubber for feeding said absorption liquid between said inner and outer tubes of said diffusion scrubber; and at least a flow passage switch valve downstream from said diffusion scrubber, said flow passage switch valve having at least three flow passages, each of which has a port, one of said ports being coupled to said diffusion scrubber;

an absorption liquid reservoir coupled to one of said ports other than said one port coupled to said diffusion scrubber, said reservoir reserving said absorption liquid for subsequent feeding of said absorption liquid through said flow passage switch valve;

a circulation flow passage for said absorption liquid, said circulation flow passage connecting among said flow passage switch valve, said absorption liquid feeding pump and said diffusion scrubber; and a non-circulation flow passage for said absorption liquid, said non-circulation flow passage connecting said absorption liquid reservoir through said flow passage switch valve and said absorption liquid feeding pump into said diffusion scrubber;

wherein said flow passage switch valve provides the current flow passage switch between said circulation and non-circulation flow passages.

2. The apparatus as claimed in claim 1, wherein said diffusion scrubber fixes said inner and outer tubes by a set of joint members provided at longitudinally opposite ends of said diffusion scrubber, an inlet port for said absorption liquid being provided at one of said opposite ends and an outlet port for said absorption liquid being provided at another of said opposite ends.

3. The apparatus as claimed in claim 1, further comprising:

a sample injection valve between upstream of said diffusion scrubber and downstream of said absorption liquid feeding pump, said sample injection valve comprising at least six flow passages, each of which has a port; and a concentration column to said sample injection valve through different ports from said ports used for coupling between said diffusion scrubber and said absorption liquid feeding pump;

wherein said sample injection valve switches between different two flow passages, in one flow passage said concentration column is incorporated into said circulation or non-circulation flow passage, in another flow passage said concentration column is isolated from said circulation or non-circulation flow passage.

4. The apparatus as claimed in claim 1, further providing a gas sampling pump at one end of said diffusion scrubber for feeding sampling gases into said diffusion scrubber.

5. The apparatus as claimed in claim 1, wherein said flow passage switch valve has four flow passages.

6. The apparatus as claimed in claim 1, wherein said flow passage switch valve has three flow passages.

7. The apparatus as claimed in claim 6, further comprising:

a defoamer upstream of said flow passage switch valve for removing any foam from said absorption liquid, said defoamer having at least three ports, a first one being used for import of said absorption liquid, a second one being used for export of said absorption liquid and a third one being used for export of said sampling gases; and a check valve at said third port for restricting flow ways of said absorption liquid into one way.

8. The apparatus as claimed in claim 7, wherein said absorption liquid reservoir is positioned at a higher level than a level of said defoamer which is positioned at a higher level than one end portion of a pipeline, an opposite end of which is connected to a gas export of said defoamer, so that there is fed from said absorption liquid reservoir into said defoamer a larger amount of said absorption liquid than an amount thereof fed by said absorption liquid pump due to siphon effect.

9. The apparatus as claimed in claim 1, wherein said absorption liquid reservoir has a cap and at least two connective ports, one port being for feeding said absorption liquid in said reserver into said non-circulation flow passage, another one being coupled a pipeline with a control valve for introducing air or an inert gas into said reservoir.

10. An apparatus for analyzing gas components comprising one or more gas collectors and a gas analyzer:

said gas collector comprising:
- a diffusion scrubber comprising an inner tube and an outer tube, said inner tube comprising a gas penetrating membrane through which sampling gases only may penetrate, wherein sampling gases flow through inside of said inner tube and an absorption liquid flows through between said inner and outer tubes so that said absorption liquid absorbs said sampling gases penetrated through said membrane from the inside of the inner tube;
- an absorption liquid feeding pump upstream from said diffusion scrubber for feeding said absorption liquid between said inner and outer tubes of said diffusion scrubber; and
- at least a flow passage switch valve downstream from said diffusion scrubber, said flow passage switch valve having at least three flow passages, each of which has a port, one of said ports being coupled to said diffusion scrubber;
- an absorption liquid reservoir coupled to one of said ports other than said one port coupled to said diffusion scrubber, said reservoir reserving said absorption liquid for subsequent feeding of said absorption liquid through said flow passage switch valve;
- a circulation flow passage for said absorption liquid, said circulation flow passage connecting among said flow passage switch valve, said absorption liquid feeding pump and said diffusion scrubber; and
- a non-circulation flow passage for said absorption liquid, said non-circulation flow passage connecting said absorption liquid reservoir through said flow passage switch valve and said absorption liquid feeding pump into said diffusion scrubber;
- a sample injection valve between upstream of said diffusion scrubber and downstream of said absorption liquid feeding pump, said sample injection valve comprising at least six flow passages, each of which has a port; and
- a concentration column connected to said sample injection valve through different ports from said ports used for coupling between said diffusion scrubber and said absorption liquid feeding pump;
- wherein said flow passage switch valve provides the current flow passage switch between said circulation and non-circulation flow passages; and said gas analyzer comprising:
- an eluate reservoir for reserving an eluate to be used for eluting sampling gas components for subsequent analysis thereof;
- an eluate pump between said sample injection valve and said eluate reservoir for feeding said eluate from said eluate reservoir into said sample injection valve, said eluate pump being coupled to a port of said sample injection valve other than the ports coupled to said diffusion scrubber and said concentration column respectively;
- a detector for detecting gas components eluted in said elution, said detector being coupled to said sample injection valve through a different port of said valve from said ports respectively coupled to said diffusion scrubber, said concentration column and said elution reservoir so as to form a gas analyzer flow passage connecting said eluate reservoir through said eluate pump and said sample injection valve into said detector:
- wherein said sample injection valve switches between two different flow passages, in one flow passage said concentration column is incorporated into an absorption liquid flow passage system, in another flow passage said concentration column is separated from said absorption liquid flow passage system.

11. The apparatus as claimed in claim 10, wherein said detector comprises a liquid chromatograph.

12. The apparatus as claimed in claim 10, wherein said detector comprises an ion chromatograph.

13. The apparatus as claimed in claim 10, wherein said diffusion scrubber fixes said inner and outer tubes by a set of joint members provided at longitudinally opposite ends of said diffusion scrubber, an inlet port for said absorption liquid being provided at one of said opposite ends and an outlet port for said absorption liquid being provided at another of said opposite ends.

14. The apparatus as claimed in claim 10, further comprising:
- a sample injection valve between upstream of said diffusion scrubber and downstream of said absorption liquid feeding pump, said sample injection valve comprising at least six flow passages, each of which has a port; and
- a concentration column connected to said sample injection valve through different ports from said ports used for coupling between said diffusion scrubber and said absorption liquid feeding pump;
- wherein said sample injection valve switches between different two flow passages, in one flow passage said concentration column is incorporated into said circulation or non-circulation flow passage, in another flow passage said concentration column is isolated from said circulation or non-circulation flow passage.

15. The apparatus as claimed in claim 10, further comprising a gas sampling pump at one end of said diffusion scrubber for feeding sampling gases into said diffusion scrubber.

16. The apparatus as claimed in claim 10, wherein said flow passage switch valve has four flow passages.

17. The apparatus as claimed in claim 10, wherein said flow passage switch valve has three flow passages.

18. The apparatus as claimed in claim claim 17, further comprising:
- a defoamer upstream of said flow passage switch valve for removing any foam from said absorption liquid, said defoamer having at least three ports, a first one being used for import of said absorption liquid, a second one being used for export of said absorption liquid and third one being used for export of said sampling gases; and a check valve at said third port for restricting flow ways of said absorption liquid into one way.

19. The apparatus as claimed in claim 18, wherein said absorption liquid reservoir is positioned at a higher level than a level of said defoamer which is positioned at a higher level than one end portion of a pipeline, an opposite end of which is connected to a gas export of said defoamer, so that there is fed from said absorption liquid reservoir into said defoamer a larger amount of said absorption liquid than an amount thereof fed by said absorption liquid pump.

20. The apparatus as claimed in claim 10, wherein said absorption liquid reservoir has a cap and at least two connective ports, one port being for feeding said absorption liquid in said reservoir into said non-circulation flow passage, another one being coupled a pipeline with a control valve for introducing an air or an inert gas into said reservoir.

21. The apparatus as claimed in claim 10, further comprising a central control system coupled to said absorption liquid feeding pump for controlling operations of said absorption liquid feeding pump, said central control system being also coupled to said eluate pump for controlling operations of said eluate pump, said central control system being also coupled to said flow passage switch valve for controlling operations of said flow passage switch valve, said central control system being also coupled to said sample injection valve for controlling operations of said sample injection valve and said central control system being also coupled to said detector for fetching detected data about sampling gas components from said detector and subsequent data processing.

22. The apparatus as claimed in claim 10, wherein there are provided a plurality of said gas collectors and wherein said sample injection valves of said gas collectors are connected in series between said eluate pump and said detector.

23. The apparatus as claimed claim 10, further comprising:

a rinse water injection valve being provided between said eluate pump and said sample injection valve, said rinsing water valve having six flow passages;

a rinse water measuring tube being coupled to said rinse water injection valve through its ports other than ports coupled respectively to said eluate pump and to said sample injection valve, said rinse water measuring tube being capable of measuring an amount of a rinse water by reserving said rinse water therein; and a rinse water feeder being coupled to said rinse water injection valve through a port other than said ports coupled respectively to said eluate pump, to said sample injection valve and to said rinse water measuring tube, said rinse water feeder feeding said rinse water to said rinse water injection valve;

wherein said rinse water injection valve switches between two different flow passages, one flow passage allowing said rinse water fed from said rinse water feeder to be charged in said rinse water measuring tube, another flow passage allowing said rinse water charged in said rinse water measuring tube to be fed to said sample injection valve.

24. The apparatus as claimed in claim 10, further comprising:

a rinse water injection valve coupled between said eluate pump and said sample injection valve, said rinse water injection valve being coupled between said diffusion scrubber and said sample injection valve, said rinsing water valve having six flow passages;

a rinse water measuring tube coupled to said rinse water injection valve through ports other than ports coupled respectively to said eluate pump and said sample injection valve and said diffusion scrubber, said rinse water measuring tube being capable of measuring an amount of a rinse water by reserving said rinse water therein; and a rinse water feeder being coupled to said rinse water injection valve through a port other than said ports coupled respectively to said eluate pump, to said sample injection valve and to said rinse water measuring tube, said rinse water feeder feeding said rinse water to said rinse water injection valve;

wherein said rinse water injection valve switches between two different flow passages, one flow passage allowing said rinse water fed from said rinse water feeder to be charged in said rinse water measuring tube, another flow passage allowing said rinse water charged in said rinse water measuring tube to be fed to said sample injection valve.

25. The apparatus as claimed in claim 10, further comprising:

a rinse water injection valve coupled between said sample injection valve and an absorption liquid import of said diffusion scrubber, said rinse water injection valve being also coupled between said flow passage switch valve and an absorption liquid export of said diffusion scrubber, said rinse water injection valve having a discharge port from which said rinse water is discharged:

wherein said rinse water injection valve switches between different two flow passages, one flow passage both connecting said sample injection valve to said discharge port and connecting said absorption liquid import to said absorption liquid export, the other flow passage both connecting said sample injection valve to said absorption liquid import and connecting said absorption liquid export to said flow passage switch valve.

* * * * *